(12) United States Patent
Kuo

(10) Patent No.: US 12,011,387 B2
(45) Date of Patent: Jun. 18, 2024

(54) DENTAL APPLIANCE FEATURES FOR PREVENTING LISPING

(71) Applicant: Align Technology, Inc., San Jose, CA (US)

(72) Inventor: Eric Kuo, San Jose, CA (US)

(73) Assignee: Align Technology, Inc., San Jose, CA (US)

( * ) Notice: Subject to any disclaimer, the term of this patent is extended or adjusted under 35 U.S.C. 154(b) by 7 days.

(21) Appl. No.: 17/341,177

(22) Filed: Jun. 7, 2021

(65) Prior Publication Data

US 2021/0290343 A1 Sep. 23, 2021

Related U.S. Application Data

(62) Division of application No. 15/829,504, filed on Dec. 1, 2017, now Pat. No. 11,026,831.

(60) Provisional application No. 62/429,548, filed on Dec. 2, 2016.

(51) Int. Cl.
*A61F 5/58* (2006.01)
*A61C 7/08* (2006.01)

(52) U.S. Cl.
CPC . *A61F 5/58* (2013.01); *A61C 7/08* (2013.01)

(58) Field of Classification Search
CPC .................................. A61C 7/08; A61C 5/58
USPC ...................................................... 600/23–24
See application file for complete search history.

(56) References Cited

U.S. PATENT DOCUMENTS

| | | | |
|---|---|---|---|
| 3,162,948 A | 12/1964 | Gerber | |
| 3,259,129 A | 7/1966 | William | |
| 3,792,529 A | 2/1974 | Goshgarian | |
| 4,592,725 A | 6/1986 | Goshgarian | |
| 4,919,612 A | 4/1990 | Bergersen | |
| 4,976,614 A | 12/1990 | Tepper | |
| 5,167,499 A | 12/1992 | Arndt et al. | |
| 5,820,368 A | 10/1998 | Wolk | |
| 6,142,780 A | 11/2000 | Burgio | |
| 6,257,239 B1 | 7/2001 | Kittelsen et al. | |
| 6,386,864 B1 | 5/2002 | Kuo | |
| 6,491,519 B1 | 12/2002 | Clark et al. | |

(Continued)

FOREIGN PATENT DOCUMENTS

CN 201101586 Y 8/2008
CN 101426449 A 5/2009
(Continued)

*Primary Examiner* — Sunita Reddy
(74) *Attorney, Agent, or Firm* — Shay Glenn LLP

(57) ABSTRACT

Dental appliances for preventing lisping. An aligner body is configured to apply orthodontic force to a patient's teeth within a dentition-receiving cavity to gradually align the patient's teeth. The dentition-receiving cavity includes a posterior teeth region having lateral walls configured to receive the patient's posterior teeth. The posterior teeth region includes occlusal cut-outs that are configured to expose occlusal surfaces of at least a portion of the patient's posterior teeth. The occlusal cut-outs allow opposing occlusal surfaces of the patient's posterior teeth to come close enough to touch each other while the device is worn over the dental arch of the patient to form an anterior seal between the patient's tongue and inner surfaces of the patient's anterior teeth in a manner as to minimize any temporary anterior bite opening, preventing lisping while the device is worn over the dental arch.

9 Claims, 23 Drawing Sheets

(56) References Cited

U.S. PATENT DOCUMENTS

| | | |
|---|---|---|
| 6,526,982 B1* | 3/2003 | Strong .................... A61F 5/566 128/848 |
| 6,783,604 B2 | 8/2004 | Tricca |
| 6,790,035 B2 | 9/2004 | Tricca et al. |
| 6,947,038 B1 | 9/2005 | Anh et al. |
| 7,104,792 B2 | 9/2006 | Taub et al. |
| 7,160,107 B2 | 1/2007 | Kopelman et al. |
| 7,168,950 B2 | 1/2007 | Cinader, Jr. et al. |
| 7,448,514 B2 | 11/2008 | Wen |
| 7,600,999 B2 | 10/2009 | Knopp |
| 7,766,658 B2 | 8/2010 | Tricca et al. |
| 7,771,195 B2 | 8/2010 | Knopp et al. |
| 7,871,269 B2 | 1/2011 | Wu et al. |
| 7,883,334 B2 | 2/2011 | Li et al. |
| 7,914,283 B2 | 3/2011 | Kuo |
| 8,235,715 B2 | 8/2012 | Kuo |
| 8,272,866 B2 | 9/2012 | Chun et al. |
| 8,303,302 B2 | 11/2012 | Teasdale |
| 8,337,199 B2 | 12/2012 | Wen |
| 8,401,686 B2 | 3/2013 | Moss et al. |
| 8,562,337 B2 | 10/2013 | Kuo et al. |
| 8,684,729 B2 | 4/2014 | Wen |
| 8,758,009 B2 | 6/2014 | Chen et al. |
| 8,886,702 B2 | 11/2014 | Hering et al. |
| 9,119,691 B2 | 9/2015 | Namiranian et al. |
| 9,326,831 B2 | 5/2016 | Cheang |
| 9,381,810 B2 | 7/2016 | Nelson et al. |
| 9,655,691 B2 | 5/2017 | Li et al. |
| 9,700,385 B2 | 7/2017 | Webber |
| 9,844,424 B2 | 12/2017 | Wu et al. |
| 10,045,835 B2 | 8/2018 | Boronkay et al. |
| 10,111,730 B2 | 10/2018 | Webber et al. |
| 10,150,244 B2 | 12/2018 | Sato et al. |
| 10,201,409 B2 | 2/2019 | Mason et al. |
| 10,213,277 B2 | 2/2019 | Webber et al. |
| 10,363,116 B2 | 7/2019 | Boronkay |
| 10,390,913 B2 | 8/2019 | Sabina et al. |
| D865,180 S | 10/2019 | Bauer et al. |
| 10,463,452 B2 | 11/2019 | Matov et al. |
| 10,492,888 B2 | 12/2019 | Chen et al. |
| 10,517,701 B2 | 12/2019 | Boronkay |
| 10,537,463 B2 | 1/2020 | Kopelman |
| 10,555,792 B2 | 2/2020 | Kopelman et al. |
| 10,588,776 B2 | 3/2020 | Cam et al. |
| 10,743,964 B2 | 8/2020 | Wu et al. |
| 10,758,323 B2 | 9/2020 | Kopelman |
| 10,781,274 B2 | 9/2020 | Liska et al. |
| 10,881,487 B2 | 1/2021 | Cam et al. |
| 10,912,629 B2 | 2/2021 | Tanugula et al. |
| 10,980,613 B2 | 4/2021 | Shanjani et al. |
| 10,993,783 B2 | 5/2021 | Wu et al. |
| 2004/0013993 A1 | 1/2004 | Ito |
| 2004/0013996 A1 | 1/2004 | Sapian |
| 2004/0166462 A1 | 8/2004 | Phan et al. |
| 2005/0014105 A1 | 1/2005 | Abolfathi et al. |
| 2005/0244768 A1 | 11/2005 | Taub et al. |
| 2006/0019218 A1 | 1/2006 | Kuo |
| 2006/0078841 A1 | 4/2006 | Desimone et al. |
| 2006/0093983 A1 | 5/2006 | Schultz |
| 2006/0115782 A1 | 6/2006 | Li et al. |
| 2006/0199142 A1 | 9/2006 | Liu et al. |
| 2008/0050692 A1 | 2/2008 | Hilliard |
| 2008/0160473 A1 | 7/2008 | Li et al. |
| 2008/0182220 A1 | 7/2008 | Chishti et al. |
| 2008/0286716 A1 | 11/2008 | Sherwood |
| 2008/0286717 A1 | 11/2008 | Sherwood |
| 2008/0289637 A1* | 11/2008 | Wyss .................... A61F 5/566 128/848 |
| 2008/0311535 A1 | 12/2008 | Andreiko |
| 2009/0208897 A1 | 8/2009 | Kuo |
| 2009/0280450 A1 | 11/2009 | Kuo |
| 2010/0055635 A1 | 3/2010 | Kakavand |
| 2010/0129763 A1 | 5/2010 | Kuo |
| 2010/0279245 A1 | 11/2010 | Navarro |
| 2011/0020761 A1 | 1/2011 | Kalili |
| 2014/0067334 A1 | 3/2014 | Kuo |
| 2014/0170591 A1 | 6/2014 | El-Siblani |
| 2014/0326253 A1 | 11/2014 | Baratier et al. |
| 2015/0257856 A1 | 9/2015 | Martz et al. |
| 2015/0265376 A1 | 9/2015 | Kopelman |
| 2015/0366637 A1 | 12/2015 | Kopelman et al. |
| 2015/0366638 A1 | 12/2015 | Kopelman et al. |
| 2016/0193014 A1 | 7/2016 | Morton et al. |
| 2016/0242870 A1 | 8/2016 | Matov et al. |
| 2017/0007359 A1 | 1/2017 | Kopelman et al. |
| 2017/0007360 A1 | 1/2017 | Kopelman et al. |
| 2017/0007361 A1 | 1/2017 | Boronkay et al. |
| 2017/0007386 A1 | 1/2017 | Mason et al. |
| 2017/0105816 A1 | 4/2017 | Ward |
| 2017/0105817 A1 | 4/2017 | Chun et al. |
| 2017/0196727 A1* | 7/2017 | Giridharagopalan ....................... A61B 5/0024 |
| 2018/0168776 A1 | 6/2018 | Webber |
| 2018/0200031 A1 | 7/2018 | Webber et al. |
| 2018/0325626 A1 | 11/2018 | Huang |
| 2019/0000592 A1 | 1/2019 | Cam et al. |
| 2019/0000593 A1 | 1/2019 | Cam et al. |
| 2019/0029775 A1 | 1/2019 | Morton et al. |
| 2019/0125497 A1 | 5/2019 | Derakhshan et al. |
| 2019/0152152 A1 | 5/2019 | O'Leary et al. |
| 2019/0192259 A1 | 6/2019 | Kopelman et al. |
| 2019/0231477 A1 | 8/2019 | Shanjani et al. |
| 2019/0262101 A1 | 8/2019 | Shanjani et al. |
| 2019/0298494 A1 | 10/2019 | Webber et al. |
| 2019/0338067 A1 | 11/2019 | Liska et al. |
| 2019/0343606 A1 | 11/2019 | Wu et al. |
| 2020/0000553 A1 | 1/2020 | Makarenkova et al. |
| 2020/0086553 A1 | 3/2020 | Mojdeh et al. |
| 2020/0100864 A1 | 4/2020 | Wang et al. |
| 2020/0100865 A1 | 4/2020 | Wang et al. |
| 2020/0100866 A1 | 4/2020 | Medvinskaya et al. |
| 2020/0100871 A1 | 4/2020 | Wang et al. |
| 2020/0155276 A1 | 5/2020 | Cam et al. |
| 2020/0188062 A1 | 6/2020 | Kopelman et al. |
| 2020/0214598 A1 | 7/2020 | Li et al. |
| 2020/0214801 A1 | 7/2020 | Wang et al. |
| 2020/0390523 A1 | 12/2020 | Sato et al. |
| 2020/0405451 A1 | 12/2020 | Lemchen |
| 2021/0078357 A1 | 3/2021 | Venkatasanthanam et al. |
| 2021/0147672 A1 | 5/2021 | Cole et al. |
| 2021/0259812 A1 | 8/2021 | O'Leary et al. |

FOREIGN PATENT DOCUMENTS

| | | |
|---|---|---|
| CN | 104000662 A | 8/2014 |
| CN | 105266907 A | 1/2016 |
| CN | 106667594 A | 5/2017 |
| DE | 102009023357 A1 | 12/2010 |
| DE | 102012023085 A1 | 5/2014 |
| KR | 20160133921 A | 11/2016 |
| WO | 2017105117 A2 | 6/2017 |

* cited by examiner

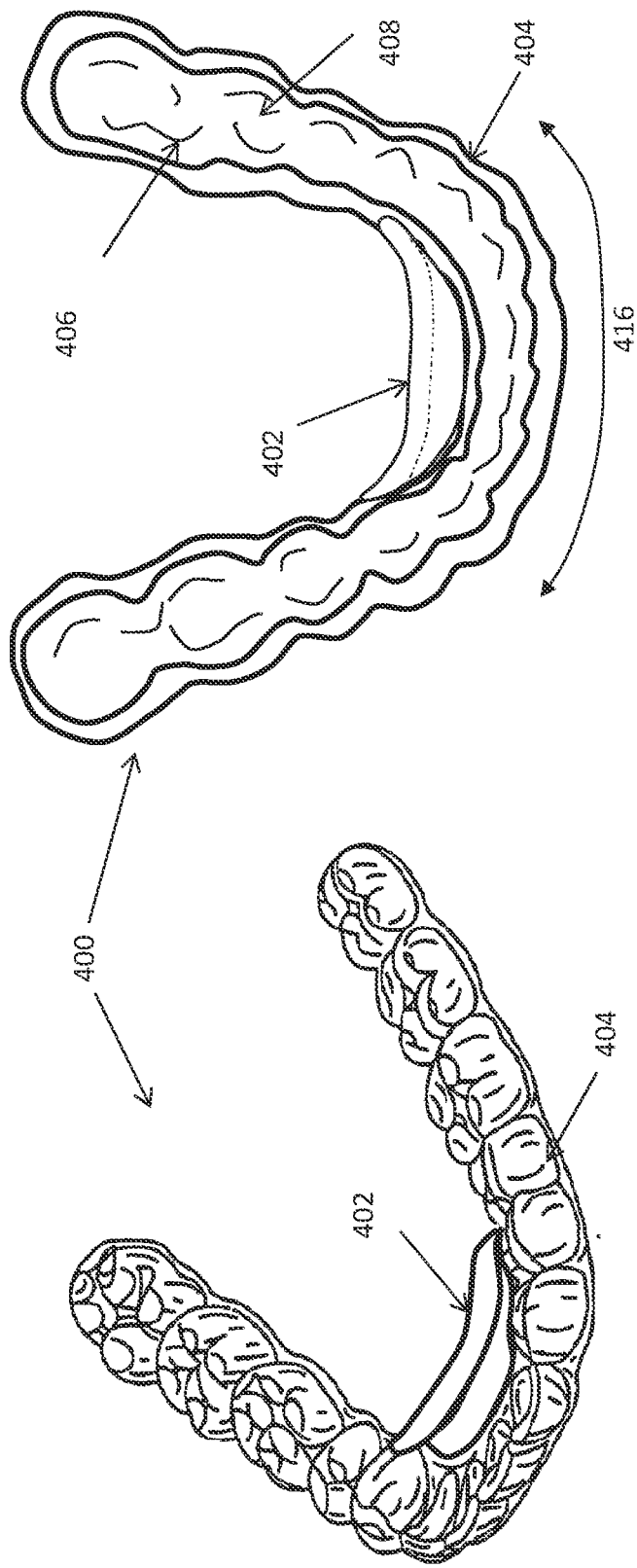
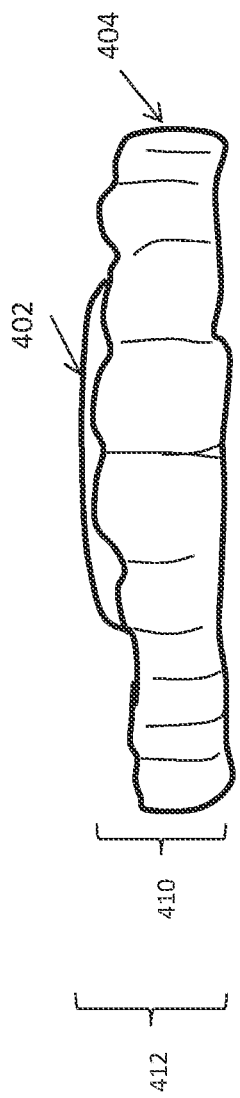
FIG. 4A
FIG. 4B
FIG. 4C

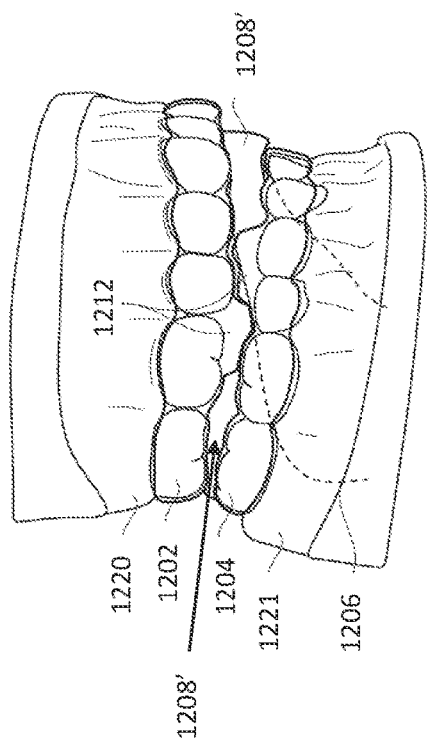
FIG. 12C
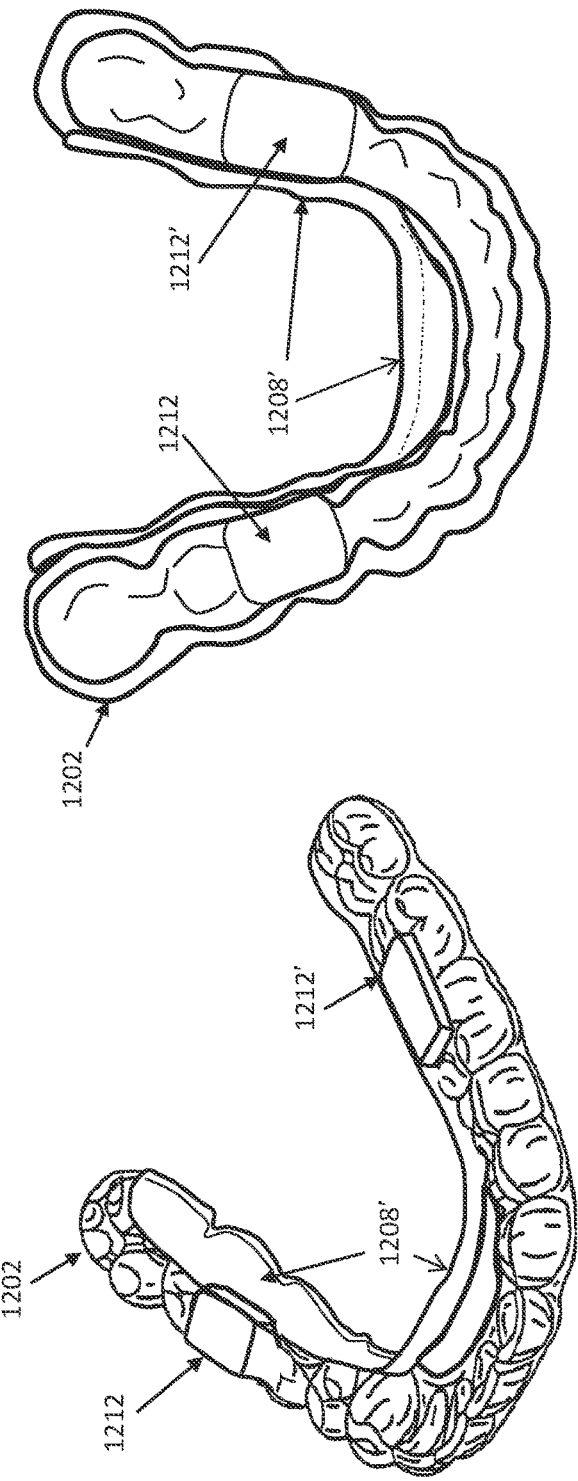
FIG. 12E
FIG. 12D

1502 — Positioning an occlusal portion of an orthodontic device over the patient's dental arch so that the patient's teeth are within a dentition cavity of the occlusal portion to apply force to the patient's teeth to align the teeth by gradually moving the patient's teeth relative to each other when the orthodontic device is worn.

1504 — While the patient is wearing the orthodontic device, a barrier portion of the orthodontic device that is positioned adjacent to a front region of the occlusal portion and extending vertically beyond the occlusal portion and away from the patient's teeth provides a sealing surface for the patient's tongue during speaking

FIG. 15

DENTAL APPLIANCE FEATURES FOR PREVENTING LISPING

CLAIM OF PRIORITY

This application is a divisional of U.S. patent application Ser. No. 15/829,504, filed on Dec. 1, 2017, titled "DENTAL APPLIANCE FEATURES FOR SPEECH ENHANCEMENT," now U.S. Pat. No. 11,026,831, which claims priority to U.S. Provisional Patent Application No. 62/429,548, titled "ALIGNER FEATURES FOR SPEECH ENHANCEMENT," filed on Dec. 2, 2016, each of which is herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

BACKGROUND

Current clear orthodontic aligners can open a patient's bite temporarily due to the thickness of the plastic trays. Because of the increased vertical dimension from the bite opening, the patient's tongue may not able to create an adequate anterior seal when certain sounds are spoken. A preferred vertical overlap of the anterior teeth is 2 to 4 mm, with less than 2 mm but greater than 0 mm being minimally acceptable. In particular, when the vertical overlap of the anterior teeth opens such that the tongue is unable to form a complete seal, the sibilants may be misarticulated, in some cases leading to lisping (or sigmatism). Inadequate vertical overlap of the posterior teeth (lateral open bite) can also contribute to a similar phenomenon stemming from the leakage of air due to an incomplete seal formed with the tongue. The inability to produce sibilant sounds properly during speech can be problematic for patients during work meetings, speaking over the phone, personal conversations, etc. As a result of this effect on speech, aligner wear compliance by the patient may be compromised, because the patients may simply leave out the aligners during work or during interactions with others in order to avoid lisping. If the amount of increased bite opening is relatively small, the tongue may adapt quickly over the course of a few weeks in order to create a better seal; however, compliance with aligner wear may be suboptimal until this time.

Some patients may naturally have a problem forming a seal between the tongue and the teeth even without a dental appliance in place, because of the presence of an anterior open bite, a lateral open bite, or both. The ability to reduce the open bite may improve the patient's speech, even if the open bite reduction is only temporary (i.e., while a dental device specifically designed for this purpose is being worn).

Described herein are orthodontic apparatuses (e.g., devices, appliances, etc.), including aligners and aligner features that may address these problems.

SUMMARY OF THE DISCLOSURE

The present application relates to an orthodontic device that may prevent, reduce, or inhibit poor speech articulation due to the inability to form an adequate seal between the tongue and the inner surfaces of a patient's teeth, which may result in lisping.

The devices may generally include an occlusal portion having a dentition-receiving cavity extending laterally in an arch and having a first vertical height, wherein the dentition-receiving cavity is configured to fit over a dental arch of a patient, the dentition-receiving cavity comprising an occlusal surface section adapted to be positioned over an occlusal surface of the patient's teeth. The device comprises a barrier portion extending laterally and adjacent to a region of the occlusal portion (e.g., a front region, a lateral region, etc.), the barrier portion having a second vertical height that is approximately the same height or a greater height than the first vertical height, wherein the barrier portion is laterally continuous to reduce or prevent air leakage therethrough, so that a patient's tongue may form a seal against the barrier portion when the patient is speaking while wearing the device.

In another aspect, the application relates to an orthodontic aligner device that prevents lisping. The device comprises an occlusal portion having a dentition-receiving cavity extending laterally in an arch and having a first vertical height, wherein the dentition-receiving cavity is configured to fit over a dental arch of a patient, the occlusal portion further configured to apply a force to a first set of teeth in the dentition-receiving cavity, the dentition-receiving cavity comprising an occlusal surface section adapted to be positioned over an occlusal surface of the patient's teeth; and a barrier portion extending laterally and adjacent to the occlusal portion, the barrier portion having a second vertical height that is greater than the first vertical height, wherein the barrier portion is laterally continuous to reduce or prevent air leakage therethrough, so that a patient's tongue may form a seal against the barrier portion when the patient is speaking while wearing the device.

In some embodiments, the barrier portion is positioned on a lingual side of the front region of the occlusal portion. The barrier portion can comprise a ridge. In some embodiments, the second vertical height of the barrier portion is more than about 0.5 mm higher than the first vertical height of the occlusal portion (e.g., greater than 0.8 mm, greater than 1 mm, between 1-6 mm, between 1-5 mm, between 1-4 mm, between 2-6 mm, between 2-5 mm, between 2-4 mm, etc.). In some embodiments, the second vertical height of the barrier portion is more than about 1 mm higher than the first vertical height of the occlusal portion. In some embodiments, the barrier portion is positioned on a buccal side of the front region of the occlusal portion. In some embodiments, the dentition-receiving cavity is configured to fit over an upper dental arch of the patient. In some embodiments, the dentition-receiving cavity is configured to fit over a lower dental arch of the patient. In some embodiments, the barrier portion is formed integrally with the occlusal portion. In some embodiments, the barrier portion is formed separately from and is attached to the occlusal portion. In some embodiments, the barrier portion is positioned lingual to the occlusal portion adjacent to a portion of the barrier portion that fits over a patient's incisors when the device is worn by the patient. In some embodiments, the barrier portion is positioned adjacent to a portion of the barrier portion that fits over a patient's incisors and canines when the device is worn by the patient. In some embodiments, the barrier extends posteriorly to create positive vertical overlap in the canine, bicuspid, and/or molar region. In some embodiments, the barrier is unilateral or asymmetric. In some embodiments, the barrier portion is curved and/or tapered. In some embodiments, the barrier portion is connected to or used in conjunction with bite ramp features used for temporary bite opening.

In another aspect, an orthodontic aligner device that prevents lisping is provided. The device comprises an aligner body having a dentition-receiving cavity extending laterally in an arch and having a first vertical height, wherein the dentition-receiving cavity is configured to fit over at least a portion of a dental arch of a patient, the aligner body further configured to apply a force to a first set of teeth in the dentition-receiving cavity, the dentition-receiving cavity comprising a plurality of upper surface sections configured to be positioned over occlusal surfaces of the patient's teeth when the device is worn over the dental arch of the patient, and a plurality of lateral wall surfaces configured to be placed in contact with sides of the patient's teeth when the device is worn over the dental arch, further comprising a first occlusal cut-out region at a first terminal end of the arch and a second occlusal cut-out region at a second terminal end of the arch, wherein the first cut-out region and the second cut-out regions are surrounded by lateral wall surfaces, with the occlusal surfaces of the patient's molars (and possibly also the premolars) exposed and able to touch the opposing arch when the device is worn over the teeth. This design may minimize the temporary anterior bite opening that can occur when orthodontic aligner appliances that cover the posterior teeth are being worn.

In some embodiments, the cut-out region extends over two or more teeth when the device is worn over the patient's dental arch. In some embodiments, the cut-out region extends over three or more teeth when the device is worn over the patient's dental arch. In some embodiments, a thickness of the occlusal surface of the device is thinner near the first and second terminal ends of the arch, and gets thicker towards a middle region between the first and second terminal ends of the arch. This middle region of the arch generally corresponds to the anterior teeth. In some embodiments, the cut-out regions extend into the lateral wall surfaces of the portion of the dentition-receiving cavity adjacent to the patient's molars when the device is worn over the dental arch. In some embodiments, the device comprises a barrier portion extending laterally adjacent to an anterior region of the aligner body, the barrier portion having a barrier vertical height that is greater than a first vertical height of the aligner body, wherein the barrier portion is laterally continuous to reduce or prevent air leakage therethrough, so that a patient's tongue may form a seal against the barrier portion when the patient is speaking while wearing the device.

In another aspect, a method of orthodontic treatment of a patient that prevents lisping is provided. The method comprises positioning an occlusal portion of an orthodontic device over the patient's dental arch so that the patient's teeth are contained within a dentition-receiving cavity of the occlusal portion, wherein, while the patient is wearing the orthodontic device, a barrier portion of the orthodontic device is positioned adjacent to a region of the occlusal portion and extends vertically beyond the occlusal portion and away from the patient's teeth, in order to provide a sealing surface for the patient's tongue during speaking.

In another aspect, another method to prevent lisping during orthodontic treatment of a patient is provided. The method comprises positioning an occlusal portion of an orthodontic device over the patient's dental arch so that the patient's teeth are contained within a dentition-receiving cavity of the occlusal portion which applies force to the patient's teeth to align the teeth by gradually moving the patient's teeth relative to each other when the orthodontic device is worn, wherein, while the patient is wearing the orthodontic device, a barrier portion of the orthodontic device that is positioned adjacent to a region (e.g., a front and/or lateral region) of the occlusal portion and extending vertically beyond the occlusal portion and away from the patient's teeth provides a sealing surface for the patient's tongue during speaking.

In some embodiments, the barrier portion extends laterally adjacent to the patient's incisors when the patient is wearing the orthodontic device. In some embodiments, the barrier portion extends in a continuous lateral surface adjacent to the patient's incisors when the patient is wearing the orthodontic device to reduce or prevent air leakage therethrough. In some embodiments, the method comprises differentially applying force to the patient's teeth to gradually move the patient's teeth relative to each other when the orthodontic device is worn. In some embodiments, the method comprises positioning a second occlusal portion of a second orthodontic device over a second dental arch of the patient so that the patient's teeth in the second dental arch are within a second dentition-receiving cavity of the second occlusal portion. In some embodiments, the method comprises positioning a second occlusal portion of a second orthodontic device over a second dental arch of the patient so that the patient's teeth in the second dental arch are within a second dentition-receiving cavity of the second occlusal portion and providing a second barrier portion of the second orthodontic device that is positioned adjacent to a second region of the second occlusal portion to provide a second sealing surface for the patient's tongue during speaking. In some embodiments, the lower jaw of the patient is able to reposition forward such that lower anterior teeth (with or without an orthodontic appliance) abut against a barrier portion located in the upper arch aligner in order to provide a sealing surface for the patient's tongue during speaking. In some embodiments, the lower jaw of the patient is able to rest against a vertical stop feature in the aligner such as a bite ramp feature, with a barrier portion located in the upper arch aligner built in to provide a sealing surface for the patient's tongue during speaking.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 4A-4D illustrate embodiments of a device having a barrier portion.

FIG. 12C is another example of a pair of upper and lower jaw appliances including bite ramps and a barrier portion to enhance speech and/or patient comfort. In FIG. 12C the barrier portion extends laterally along the lingual side of the upper aligner, adjacent to and on either side of the bite ramp(s).

FIGS. 12D and 12E illustrate front perspective and top bottom views, respectively, of the upper jaw appliance (which may be configured as an aligner). In FIG. 12D, the bite ramps (e.g., bite supporting structures) are integrated into the occlusal surface of the apparatus and a barrier region extends adjacent to the majority of the lingual side of the appliance to prevent air from escaping. The barrier region may have a height that is approximately the same or larger than the maximum height of the bite ramp(s). The dental appliance on the opposite side may be configured or otherwise adapted to allow the barrier region to seal any air leak between and/or over the occlusal surface(s) of the apparatuses. In FIG. 12E, the top view shows the barrier region is configured as a single barrier region extending from one side of the arch (adjacent to the rear molars) to the opposite side of the arch.

FIG. 13A shows an aligner with a tapered barrier portion in the upper aligner to provide a seal against lateral anterior air leakage when the upper bite ramps are engaged by the lower anterior dentition, especially when a deep Curve of Spee is present. FIG. 13C has an anterior barrier portion in the upper aligner to provide an anterior seal when anterior lingual bite ramps are engaged by the lower dentition.

FIG. 15 illustrates another embodiment of a method of orthodontic treatment.

In FIG. 18, the apparatus includes an upper and a lower orthodontic appliance; the barrier portion is on the upper appliance, however it may be positioned on the lower appliance. The upper and lower appliances in this example each include a pair of wings ("precision wings") that laterally interact with each other to engage with each other to reposition the patient's mandible (e.g., as part of a mandibular repositioning apparatus).

In FIG. 19A, the apparatus is one in a series of sequential palatal expanders that may be secured to the patient's upper arch through the dentition-receiving cavity formed on either side of the device; the dentition-receiving cavity includes a left dentition-receiving cavity portion and a right dentition-receiving cavity portion that are connected by a palatal region that is configured to be positioned adjacent to the patient's palate. Each device in the series of sequential expanders compresses in the transverse dimension enough during activation to engage the inner (lingual) surfaces of the posterior teeth, thereby transferring any expansion forces in the appliance through the posterior teeth to the palatal bone structures. In FIG. 19B, the apparatus of FIG. 19A is configured to include a front-facing (anterior) barrier region that may prevent lisping. The barrier region may be connected to an extension that extends from the palatal region.

DETAILED DESCRIPTION

Described herein are apparatuses including orthodontic devices that may prevent, reduce or inhibit sigmatism, or poor speech articulation of sibilants due to the inability of a patient's tongue to form a complete seal with the back of their teeth which results in lisping. Although the apparatuses and methods described herein are generally directed towards dental appliances, e.g., including, but not limited to aligners for treating teeth misalignment; any of these apparatuses and methods may be used for any other dental or orthodontic device, to improve speech when wearing such devices; furthermore, any of these apparatuses and methods may be used exclusively to treat existing patient miss-articulation (i.e., lisping). For example, these apparatuses may be configured as speech therapy devices. Examples of other appliances that may be configured or adapted to prevent speech problems and/or enhance comfort as described herein may include palatal expanders, mandibular advancement apparatuses, and the like. Any of the features shown herein for any specific appliance (e.g., aligners) may be used as part of any other dental appliance.

Figure 1:
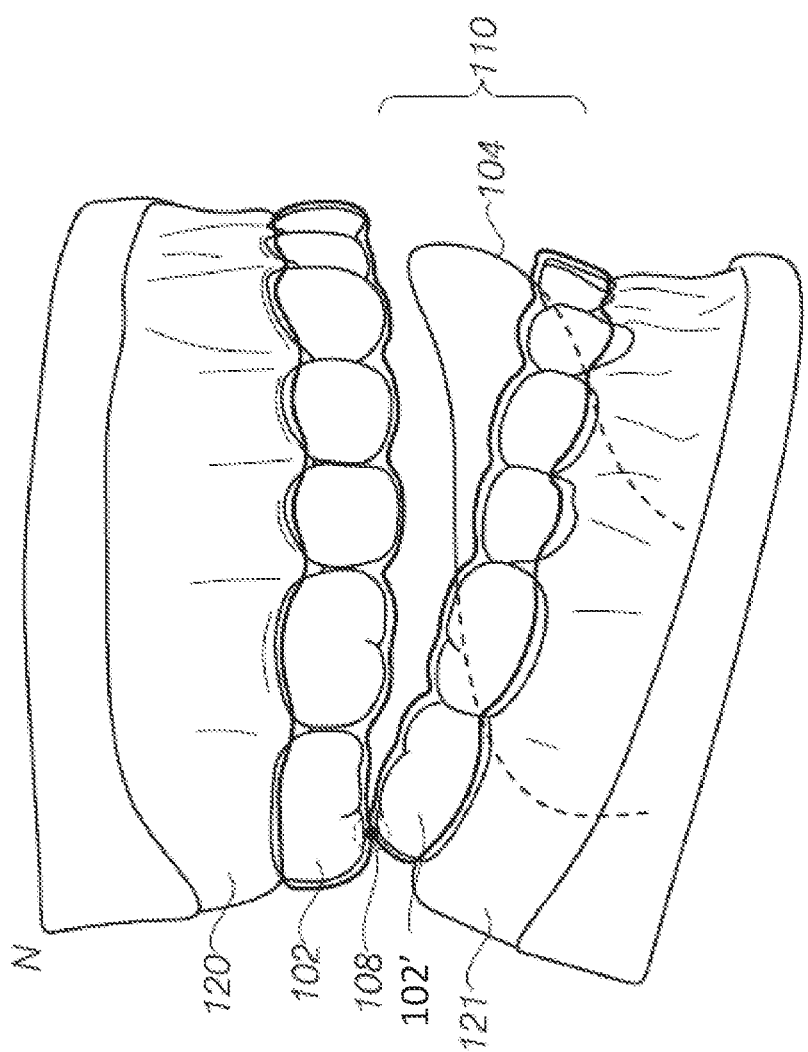
FIG. 1 illustrates a temporary bite opening effect by the use of aligners. There is a point of contact in the terminal regions of the arches due to the occlusal thickness of the aligners.

For example, disclosed herein are apparatuses and methods for addressing speech alterations caused by orthodontic appliances. FIG. 1 illustrates an example of an upper aligner 102 and a lower aligner 102'. An aligner, such as the shell type aligners shown in FIG. 1, can temporarily open the bite due to the thickness of the aligner on the occlusal surface of the teeth. In FIG. 1, a posterior contact 108 leads to an anterior opening 110. The opening 110 (which may be smaller than that illustrated in this example) can prevent the patient's tongue 104 from creating an adequate anterior seal when certain sounds are spoken, causing misarticulations. If patients are less likely to talk during the day or are less concerned about being embarrassed when speaking while wearing aligners, they are more likely to be compliant and wear the devices during their everyday social activities regardless of whether they lisp. If however, they need to talk without lisping or are embarrassed because they are lisping with the aligners in place, they are more likely to leave the aligners out during the day and only wear them when they are not interacting with others. This inconsistent usage may result in suboptimal orthodontic treatment results. Similar issues may occur with a single aligner or with other orthodontic appliances.

One way to address this problem is to reduce the thickness in the aligner which is increasing the vertical dimension and causing the bite to open. For example, thinning or removing portions of the aligner in the areas covering the posterior teeth (by creating occlusal windows, for example) can allow the back teeth to come closer together (or touch) in order to let the front portions come closer together, thereby reducing the impact of increasing the vertical dimension. For patients with a high mandibular plane angle, any increase in the vertical dimension of the posterior teeth results in a magnified increase in the anterior vertical dimension. In other words, the change in the anterior is not necessarily 1:1 with the vertical change in the posterior, and may be a multiple instead (e.g., 2× or 3×).

Figure 2B:
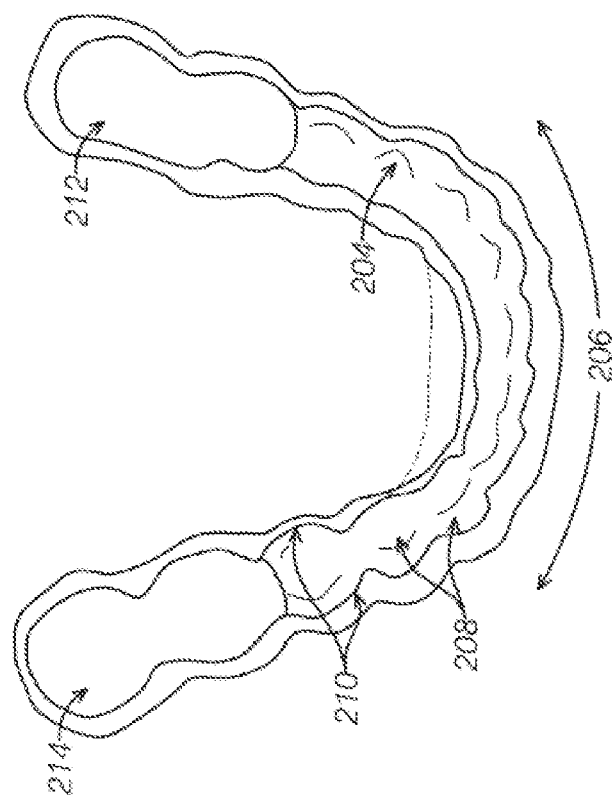
FIGS. 2A and 2B illustrate an embodiment of an aligner having occlusal windows in the terminal regions of the arch. The portions covering the molars have been removed.
Figure 2A:
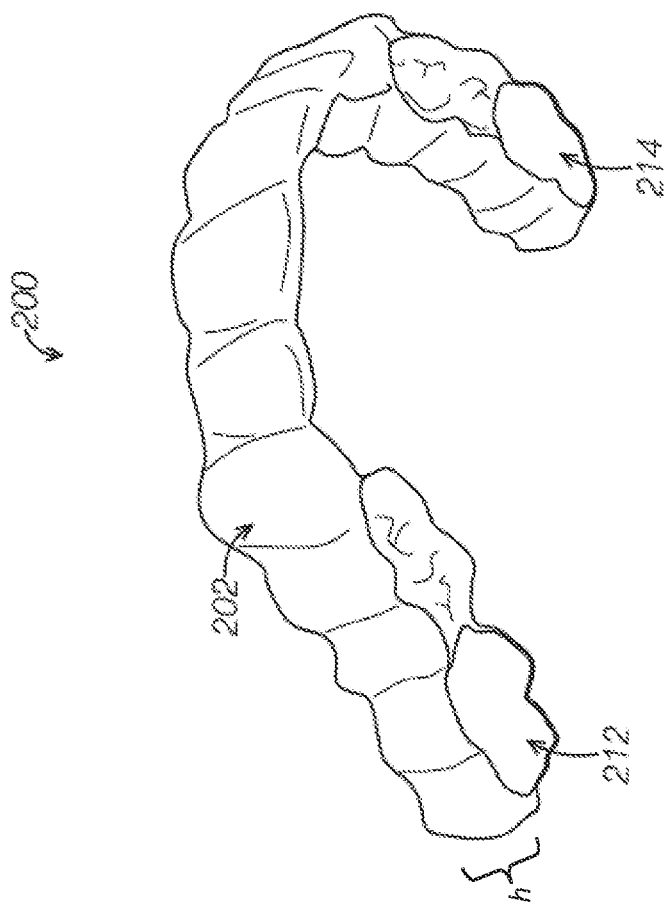

FIGS. 2A and 2B illustrate an embodiment of a device having occlusal windows. FIG. 2A illustrates a perspective view of an aligner 200 comprising an aligner body 202. As shown in the bottom view of FIG. 2B, the aligner body 202 has a dentition-receiving cavity 204 extending laterally in an arch, as shown by arrow 206 and having a first vertical height, h. The dentition-receiving cavity 204 is configured to fit over at least a portion of the dental arch. The aligner body 202 may be configured to apply a force to a first set of teeth in the dentition-receiving cavity 204. The dentition-receiving cavity 204 comprises a plurality of upper surface sections 208 configured to be positioned over the occlusal surfaces of the patient's teeth when the device is worn over the dental arch of the patient. These sections may divide the body region 202 into a plurality of (in this example, laterally contiguous) chambers each substantially conforming to individual teeth. In some variations the dentition-receiving cavity may be separate sub-regions (e.g., on either side of the arch). Alternatively or in addition, the dentition receiving cavity may include a gap or space where a tooth is missing; in some variations the body 202 is configured to attach to just a portion of the patient's dental arch (e.g., the molar/pre-molar region, etc.). The dentition-receiving cavity 204 may comprise a plurality of lateral wall surfaces 210 configured to be placed in contact with surfaces of the patient's teeth when the device is worn over the dental arch. The dentition-receiving cavity 204 in this example includes a first cut-out region 212 at a first terminal end of the arch and a second cut-out region at a second terminal end (e.g., posterior ends) of the arch. The first and second cut-out regions are surrounded by lateral wall surfaces and expose the occlusal surfaces of the patient's molars when the device is worn over the dental arch. The occlusal window can extend over two or more teeth (e.g., all the molars) or three or more teeth. In some embodiments, a thickness of the occlusal surface sections is thinner near the first and second terminal ends of the arch and becomes thicker towards the anterior region of the arch. The cut-out regions or windows can extend into the lateral wall surfaces of the portion of the dentition-receiving cavity adjacent to the patient's molars.

Figure 3A:
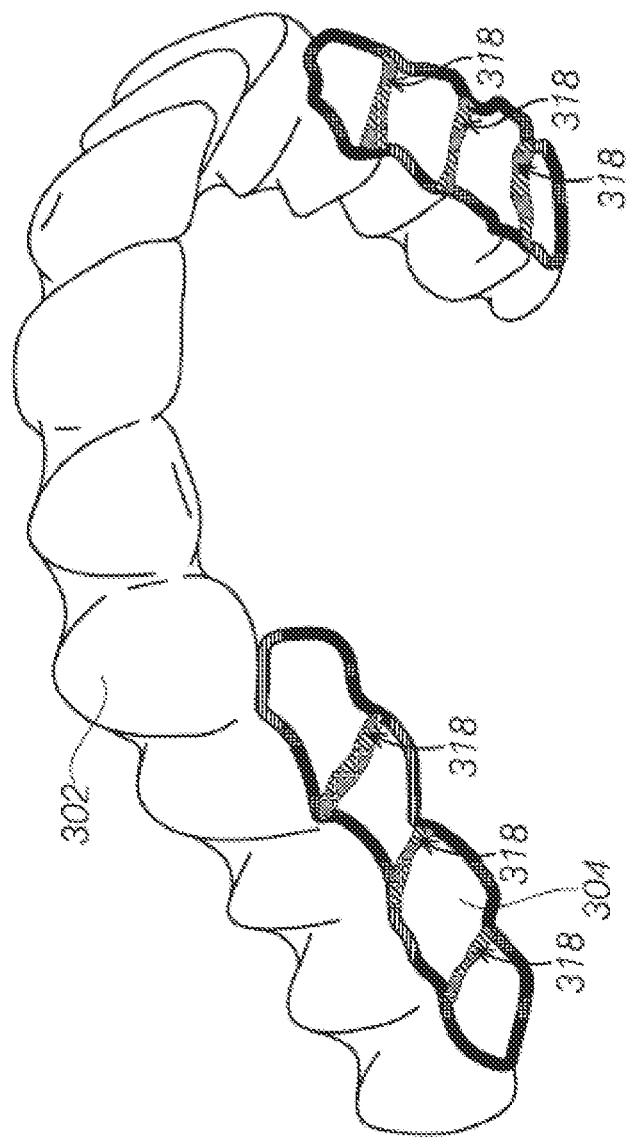
FIGS. 3A and 3B illustrate additional embodiments of aligners having occlusal windows. Portions of the aligner (on the occlusal surfaces) over both the molars and the premolars have been removed. Some occlusal regions in between the teeth have not been removed in order to provide crossbeam-like structural supports between the buccal and lingual walls of the plastic appliance (interproximal cross supports).
Figure 3B:
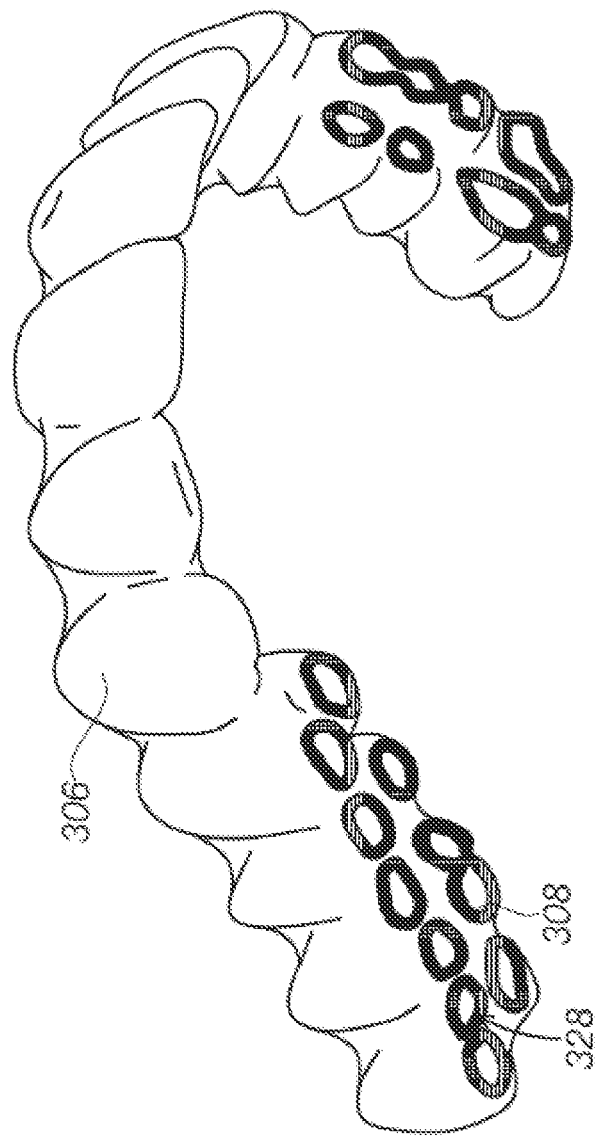

FIGS. 3A and 3B show additional embodiments of an aligner comprising occlusal windows or cutouts. As shown in FIG. 3A, the cutouts include interproximal supports 318 between buccal and lingual surfaces. The aligner 302 comprises occlusal windows 304 or cutouts over the occlusal surfaces of the back 4 teeth on each terminal end of the arch. In some embodiments, the occlusal window can be positioned over 1, 2, 3, 5, 6, or more teeth of the dental arch. The occlusal window can be positioned at a terminal end of the dental arch. In some embodiments, the occlusal window is spaced away from a terminal end of the dental arch. The aligner can comprise 1, 2, 3, 4, or more occlusal windows positioned along the aligner body.

In some cases, removal of too much of the occlusal portion can reduce rigidity of the aligner. Thus, in some variations, only the cusp tips or occlusal portions may be removed, leaving the interproximal cross supports 328 in place, as shown in FIG. 3B. Alternatively or additionally, these cross supports may be reinforced.

An additional and/or alternative solution may include a barrier (barrier region) in the anterior (and in some variations lateral) portion(s) of the aligner that provides a similar or decreased vertical dimension to what the patient had prior to wearing the aligners, so that the tongue is able to form a similar or better anterior seal while the aligners are being worn. In this manner, the problem of the lisp is reduced or eliminated and patients may be more likely to wear the aligners during the day and during social settings.

In some embodiments, for small increases in vertical dimension, the feature may not be needed, but for patients with shallow overbite, open bite, patients with Class II or Class III overjet, or patients with occlusal features in the aligner that prevent them from closing down into maximum intercuspation, the need for an anterior seal becomes greater.

The anterior seal can be facilitated by providing a barrier that helps the tongue reduce or prevent air leakage so that lisping during speech is reduced or eliminated. This barrier can comprise a protrusion that spans in the mesial-distal direction along the arch, across several teeth and positioned either on the buccal or lingual of the teeth, depending on the arch. This feature may also be used in the posterior portion of the aligner for patients with lateral open bites, where air leakage during speech occurs in the lateral or posterior-lateral regions of the arch. If the air leakage is occurring laterally (e.g., near the canines and premolars), the desired outcome may be accomplished with a barrier which creates a lateral seal with the tongue.

Figure 4D:
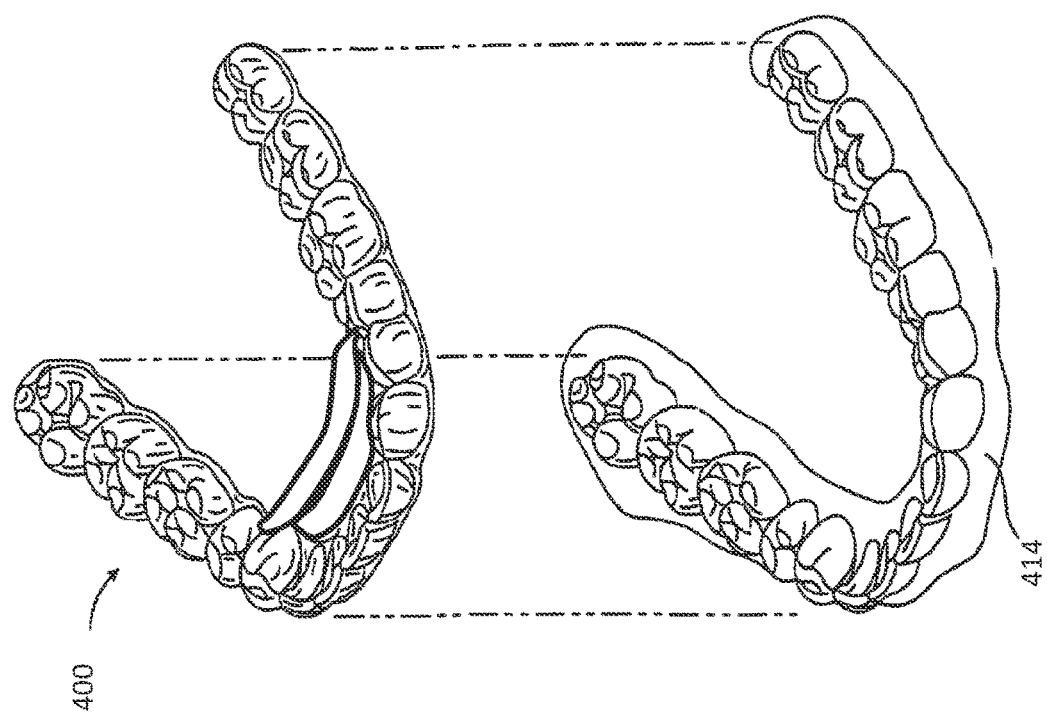

FIGS. 4A-D illustrate an embodiment of an orthodontic appliance (in this example, an aligner) 400 comprising a barrier portion 402. As shown in the top perspective view of FIG. 4A and the bottom view of FIG. 4B, the aligner comprises an occlusal portion 404 having a dentition-receiving cavity 406 extending laterally in an arch as shown by arrow 416. The occlusal portion has a first vertical height 410, as shown in the front view of FIG. 4C. The dentition-receiving cavity 404 is configured to fit over a dental arch of a patient. The dentition-receiving cavity comprises an occlusal surface section 408 adapted to be positioned over an occlusal surface of the patient's teeth. The aligner 400 also comprises a barrier portion 402 extending laterally and adjacent to a region of the occlusal portion 404. The barrier portion has a second vertical height 412 that may be at approximately the same or greater height (e.g., 0.5 mm greater, 1 mm greater) than the first vertical height 410. The barrier portion is laterally continuous to reduce or prevent air leakage there through, so that a patient's tongue may form a seal against the barrier portion when the patient is speaking while wearing the device. FIG. 4D shows the aligner 400 fitting over a patient's dental arch 414. In any of these variations the height of the barrier region may be approximately 1× or greater (e.g., 1.01×, 1.02×, 1.03×, 1.04×, 1.05×, 1.1×, 1.15×, 1.2×, 1.25×, 1.3×, 1.35×, 1.4×, 1.45×, 1.5×, etc. or greater) the height of the maximum vertical height of the appliance. The barrier region may have any lateral extent, and may typically extend along the distal (anterior) region (e.g., adjacent to the anterior teeth). For example, the barrier region may extend adjacent to the entire dental arch (e.g., adjacent to the incisors, from canine to canine, from premolar to premolar, from molar to molar, etc.).

Figure 5:
FIG. 5 illustrates an example of a tongue crib appliance 501 which is typically used to prevent the tongue from pushing the anterior teeth forward.

A side benefit of the barrier feature is that orthodontic forces on the teeth which come from the tongue pushing out the teeth bucally/facially may be reduced. The barrier feature may employ the same principle as a "tongue crib" (see, e.g., FIG. 5) for tongue thrust correction; but, unlike a tongue crib 501 which is open and made of wire, the feature claimed is continuous laterally to reduce or restrict the air flow, and allow seal to be made, which may be helpful for speech articulation. If mild air flow is desired for improved salivary circulation or improved air circulation during breathing, perforations or other surface alterations like channels or ridges may be added to the feature. Here, any perforations need to be small enough so as not to disrupt the primary objective of creating an adequate barrier seal with the tongue during speaking in order to avoid lisping.

The following figures depict various embodiments of appliances with barrier features. Unless described otherwise, the appliances described below may comprise occlusal portions and dentition-receiving cavities as described with respect to FIGS. 4A-4D, above. Furthermore, a 'front portion' of an occlusal portion with a dentition-receiving cavity fitting over the dental arch may refer to the area near the canines and incisors, but may refer to a smaller (e.g., not extending past the incisors) or greater (e.g., extending past the canines) region than that. The 'front portion' of an occlusal portion with a dentition-receiving cavity fitting over the dental arch may refer to the area near the front 2-4 teeth, 2-6 teeth, or 2-8 teeth.

Figure 6:
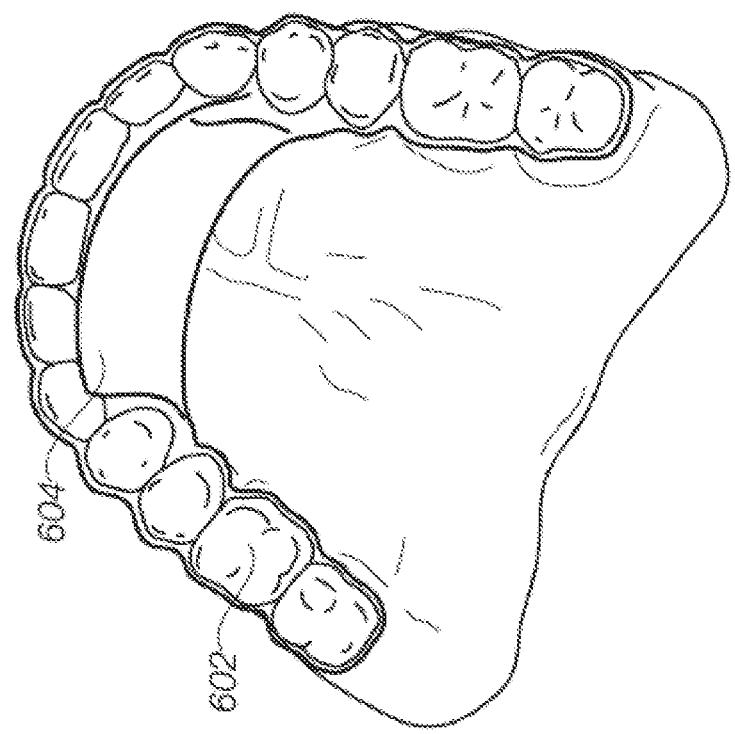
FIG. 6 schematically illustrates an embodiment of an upper aligner having a barrier feature.

FIG. 6 illustrates a bottom view of an embodiment of an upper aligner comprising a barrier feature 604 positioned proximate to a front portion of an occlusal portion 602 of the aligner. The barrier feature 604 comprises a continuous ridge in the aligner for the purpose of creating an anterior seal with the tongue in order to reduce or prevent air leakage during speaking.

Figure 7:
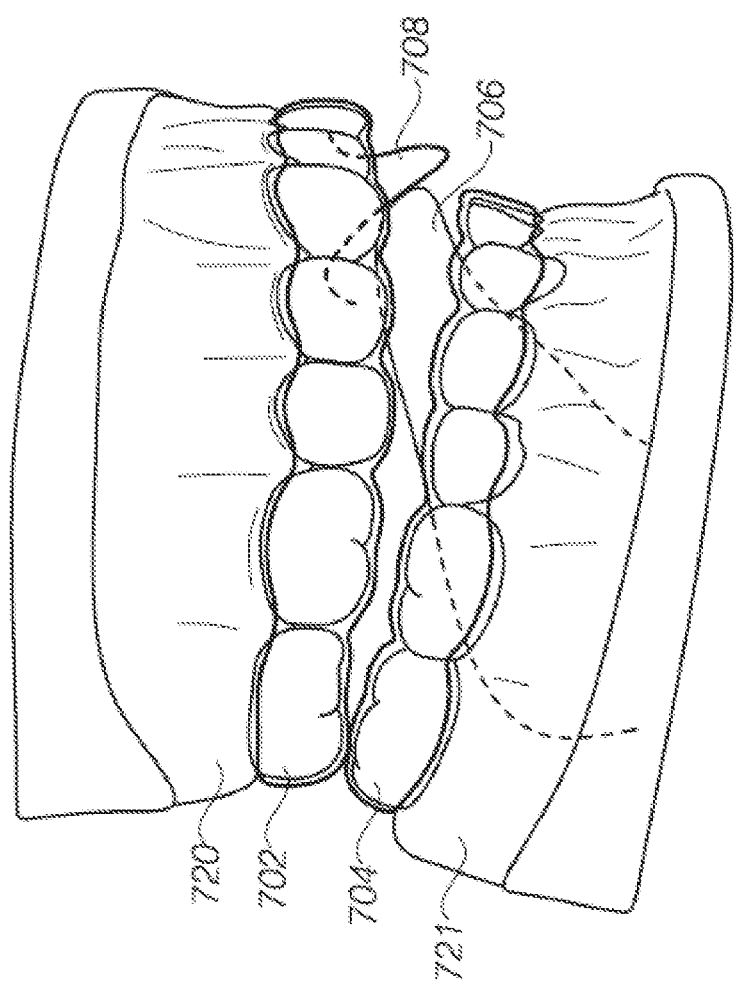
FIG. 7 illustrates embodiments of upper and lower aligners, the upper aligner having a barrier portion. The lower aligner may come into close proximity of the upper aligner in the patient's existing bite relationship, or after the patient repositions the lower jaw forward. This configuration may be useful if a patient has an excessive overjet which leads to a large anterior opening.
Figure 17B:
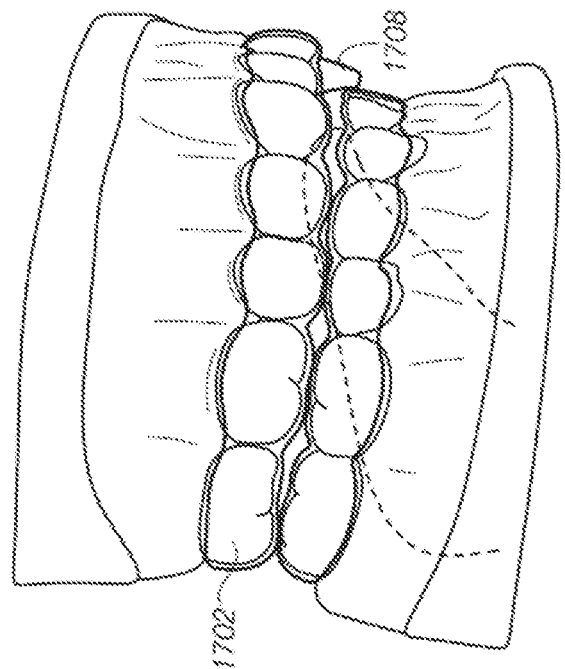
FIGS. 17A and 17B illustrate an upper aligners having a barrier portion similar to that shown in FIG. 7, in which the lower jaw (which may or may not have an aligner) may slide forward to a forward-repositioned location (shown in FIG. 17B) whereby a reduced anterior gap is created between the upper barrier and the lower teeth.
Figure 17A:
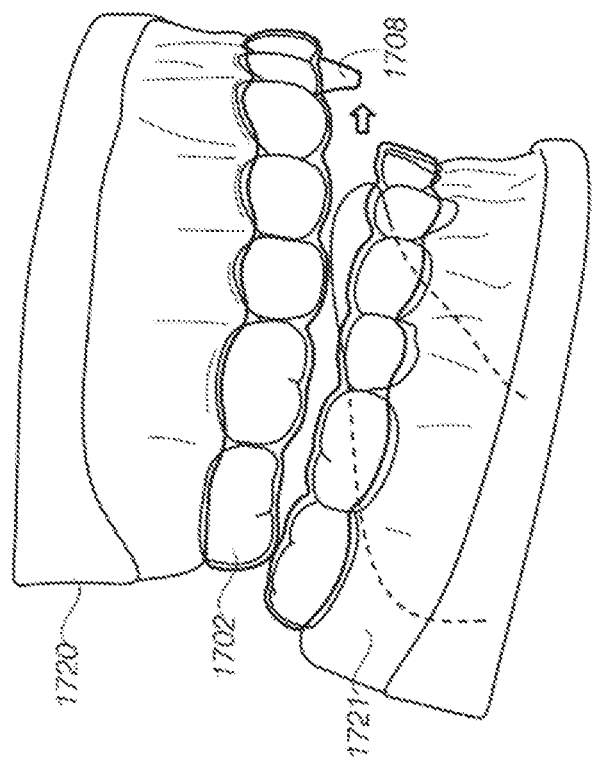

FIG. 7 illustrates a side view cross-section of an embodiment of an aligner comprising an upper aligner 702 and lower aligner 704, wherein the upper aligner comprises a barrier portion 708 and being worn by a patient. The upper aligner is shown on a model of the upper jaw teeth 720; the lower aligner is shown on a model of the lower jaw teeth 721. The barrier portion 708 is positioned proximate to a front portion of the upper occlusal portion. The barrier portion 708 comprises a mesial-distal barrier, in this embodiment positioned lingual to the dentition, which creates a barrier with the lower anterior teeth so that air leakage is reduced or eliminated when the patient speaks. FIG. 7 depicts the tongue 706 encountering the barrier portion 708. While FIG. 7 shows a lingual positioning for the barrier portion 708, buccal positioning is also possible. As mentioned above, the lower jaw of the patient may be able to reposition forward such that lower anterior teeth (with or without an orthodontic appliance) abut against a barrier portion located in the upper arch aligner in order to provide a sealing surface for the patient's tongue during speaking. This is illustrated, for example, in FIGS. 17A and 17B. In this example, similar to that shown in FIG. 7, an upper aligner 1702 includes a barrier portion 1708 lingual to the upper anterior teeth and is shown on the upper jaw 1720. The lower jaw 1721 sliding forward into a forward-repositioned location whereby a reduced anterior gap is created between the upper barrier 1708 and the lower teeth 1721.

Figure 8:
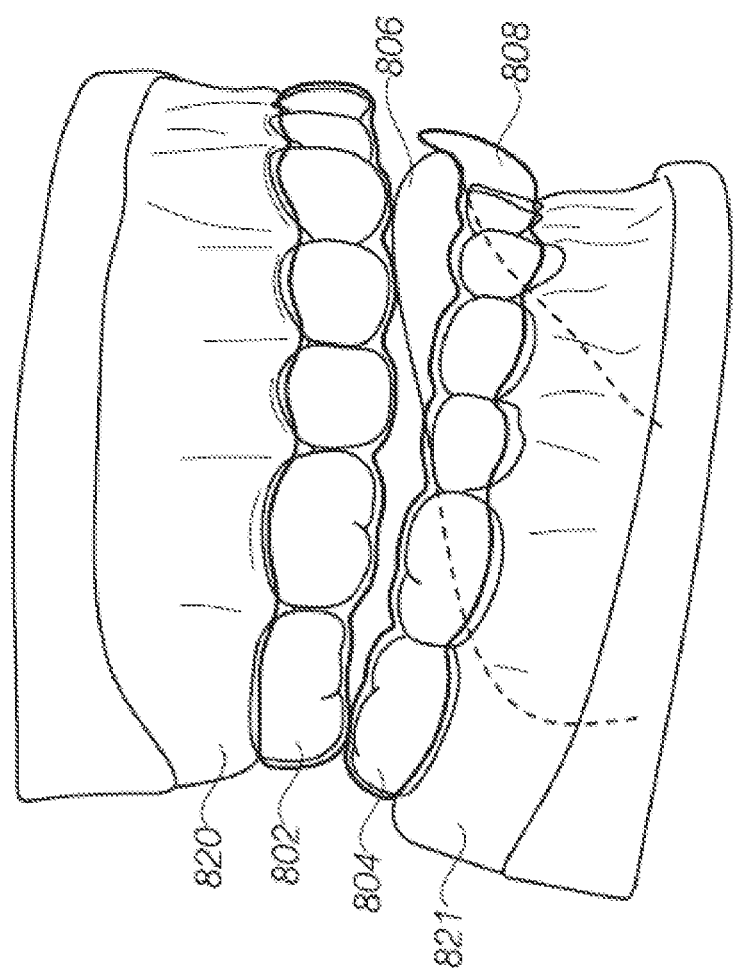
FIG. 8 illustrates embodiments of upper and lower aligners, the lower aligner having a barrier portion. This configuration may be useful if a patient has an excessive overjet which leads to a large anterior opening.

FIG. 8 illustrates a side view cross-section of an embodiment of an aligner comprising an upper aligner 802 and a lower aligner 804, the lower aligner 804 comprising a barrier portion 808. The upper aligner is shown on a model of the upper jaw teeth 820; the lower aligner is shown on a model of the lower jaw teeth 821. The barrier portion 808 is positioned near a front portion of an occlusal portion of the lower aligner 804 (a proximate or adjacent to the portion covering the canines and/or incisors). The barrier portion 808 comprises a mesial-distal barrier along the arch positioned near or on the dentition, which creates a barrier with the upper anterior teeth so that air leakage is reduced or eliminated when the patient speaks. FIG. 8 shows the tongue 806 encountering the barrier portion 808. The barrier portion 808 may typically be positioned lingually in the upper arch, particularly for patients with excessive overjet, but buccal positioning in the lower arch is also contemplated as shown in FIG. 8. In some embodiments, a lower barrier portion 808 may be useful if an upper barrier portion is less desirable (e.g., aesthetically undesirable).

Figure 9:
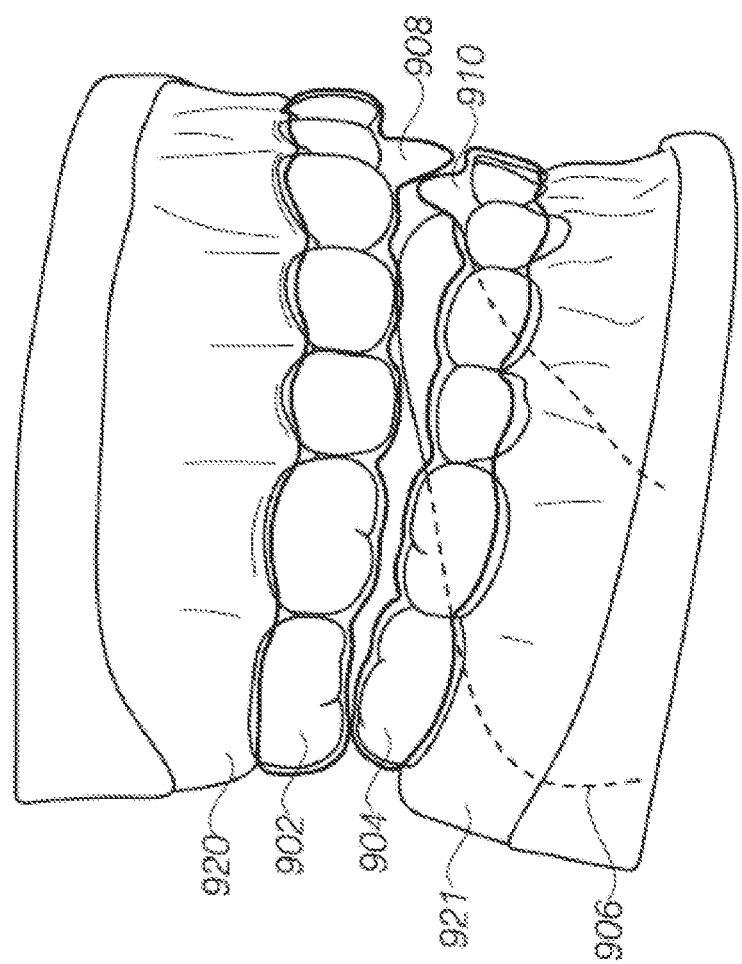
FIG. 9 illustrates embodiments of upper and lower aligners both having barrier portions. The barrier positions may come into close proximity in the patient's existing bite relationship, or after the patient repositions the lower jaw forward. This configuration may be necessary if a patient has an excessive overjet which leads to a large anterior opening, and/or if a patient has an anterior open bite which cannot be sealed by only one barrier alone.

FIG. 9 illustrates an embodiment of an upper aligner 902 comprising an upper barrier portion 908 and a lower aligner 904 comprising a lower barrier portion 910. The upper aligner is shown on a model of the upper jaw teeth 920; the lower aligner is shown on a model of the lower jaw teeth 921. One barrier in each arch may be needed if the anterior vertical dimension is excessive (in severe anterior open bite patients, for example) whereby the barrier height needed is greater than what is practical or possible to manufacture into a single aligner. The barrier portions 908, 904 may be positioned towards a front portion of their respective occlusal portions. In some embodiments, one or both of the barrier portions are positioned away from the front portion of their respective occlusal portions. Both of the barrier portions 908, 910 may be positioned lingually. In some embodiments, one barrier portion can be positioned lingually and the other buccally. In some embodiments, both barrier portions are positioned buccally, but for esthetic reasons, typically this configuration would more likely be used in the case of patients with lateral open bites. FIG. 9 shows the tongue 906 encountering the barriers 908, 910.

Figure 10:
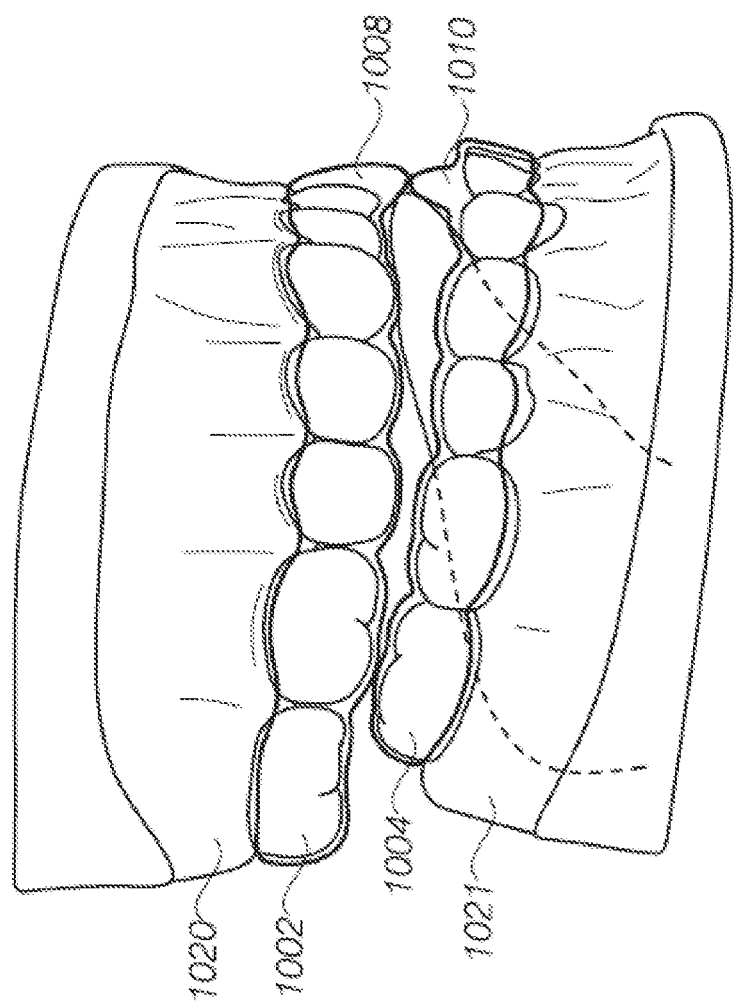
FIG. 10 illustrates embodiments of upper and lower aligners having barrier portions. This configuration may be useful if a patient has a negative overjet which leads to a large anterior opening.

In some embodiments, the barrier feature is lingually positioned on the lower arch of the aligner or buccally located on the upper arch of the aligner. Such embodiments may be appropriate for patients with Class 3 bite relationships, in which the lower arch is forward of the upper jaw position in a negative overjet relationship. FIG. 10 depicts an embodiment of an upper aligner 1002 with an upper barrier portion 1008 and a lower aligner 1004 with a lower barrier portion 1010. The barrier portions 1008, 1010 are positioned proximate or adjacent to a front portion of their respective aligner's occlusal portion. The upper barrier portion 1008 is positioned buccally, and the lower barrier portion 1010 is positioned lingually. This configuration may not be esthetically feasible in the upper arch, so having the feature present only in the lower arch may be required for Class 3 patients with significant negative overjet. The upper aligner is shown on a model of the upper jaw teeth 1020; the lower aligner is shown on a model of the lower jaw teeth 1021.

Figure 11:
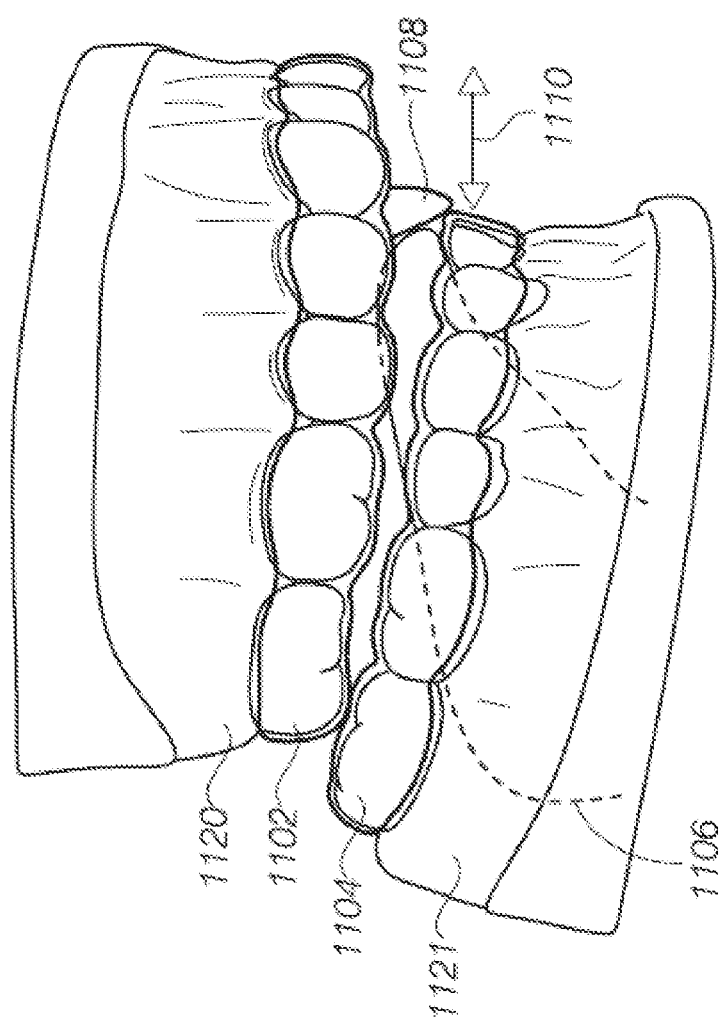
FIG. 11 illustrates embodiments of an upper and lower aligner, the upper aligner having a barrier portion. This configuration may be useful if a patient has an excessive overjet which leads to a large anterior opening, particularly if the patient is unable to sufficiently advance the lower jaw forward to create an adequate anterior seal with the tongue.

FIG. 11 shows an embodiment of an upper aligner 1102 and a lower aligner 1104, the upper aligner 1102 comprising a barrier portion 1108. The barrier portion 1108 is positioned toward the front of an occlusal portion of the upper aligner 1102 and is positioned lingually or closer to the palatal region. Such an embodiment can be appropriate for Class 2 patients with excessive overjet 1110, particularly if the patient's lower jaw is no longer growing or if the jaw is unable to reposition forward into a stable Class 1 bite relationship. The barrier portion may be positioned closer to or even on the palatal region. FIG. 11 shows the tongue 1106 encountering the barrier portion 1108. The upper aligner is shown on a model of the upper jaw teeth 1120; the lower aligner is shown on a model of the lower jaw teeth 1121.

Figure 12A:
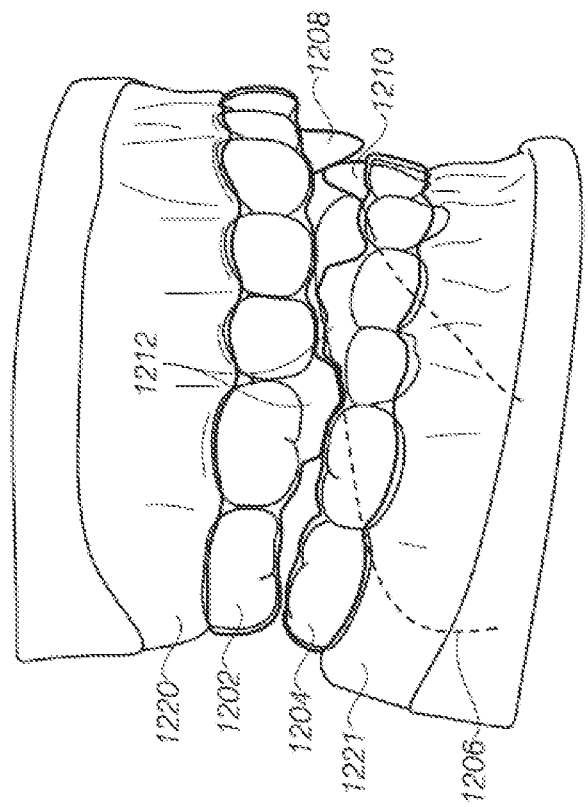
FIGS. 12A and 12B illustrates embodiments of upper and lower aligners with jaw repositioning features in the upper and lower arches and also having a barrier portion in the upper aligner (FIG. 12A) or in both the upper and lower aligners (FIG. 12B).
Figure 12B:
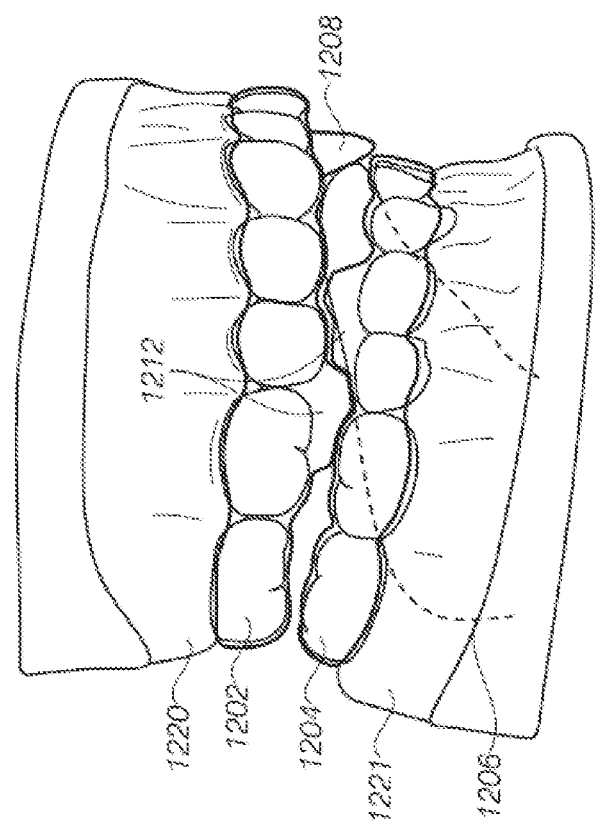

Some embodiments of aligners comprise aligner features which open the patient's bite. In such embodiments, an anterior seal may become even more critical, because of the temporary anterior open bite intentionally created when the aligners are worn. FIGS. 12A and 12B depict embodiments of an upper aligner 1202 having an upper barrier portion 1208, and in FIG. 12B and upper 1208 and a lower aligner 1204 having a lower barrier portion 1210. The aligners comprise bite repositioning features 1212 (e.g., twin block features). FIGS. 12A and 12B, respectively, show the tongue 1206 encountering the barrier portions 1208, 1210. The upper aligner is shown on a model of the upper jaw teeth 1220; the lower aligner is shown on a model of the lower jaw teeth 1221.

As mentioned above, any of the apparatuses (e.g., appliances, including but not limited to aligners) described herein may include a barrier region (or multiple barrier regions) that extend laterally along the side, e.g., adjacent to the premolars and/or molars. These apparatuses may therefore prevent air leakage from the sides and/or allow sealing by the tongue along these lateral side regions. In apparatuses, such as the example shown in FIG. 12A-12B, that may induce or address a lateral open bite, a lateral lingual or buccal barrier may be include to reduce or prevent leakage. For example, in FIGS. 12C to 12E the barrier region extend adjacent to the majority of the apparatus. For example, in FIG. 12C the apparatus includes an upper appliance 1202 and a lower appliance 1204 similar to those shown in FIG. 12A-12B. In FIG. 12C, the barrier portion 1208' is not limited to the anterior portion, but extends long both sides of the appliance (e.g., the upper and/or lower appliance). This may prevent air leakage from the sides of the appliance(s). Any of these apparatuses may be included along with an occlusal stop so that there is a resting position in which the appliance sits on the back teeth (e.g. molars).

In FIG. 12C, as shown in FIG. 12A-12B, the bite repositioning features 1212 on the upper and lower appliances may limit the closure (intercuspation) of the teeth on the upper and lower arches; in any such variations in which the bite is modified, a barrier region may be included. FIG. 12D, for example, illustrates an example in which a barrier region 1208' extends lateral from the right rear molar to the left rear molar along the entire lingual side, and adjacent to the bite repositioners 1212, 1212'. The height of the barrier region is typically the same or larger than the maximum height of these bite repositioners; the height of the barrier region may vary along the length. The barrier region may be positioned laterally on the lingual side (as shown in FIGS. 12D and 12E) or on the buccal side. The barrier may act as a shield, for example (e.g., a lingual shield), preventing the tongue from interacting with the spacer(s) and/or the appliance. In FIG. 12E, the top view shows the appliance in which the barrier region 1208' is recessed slightly lingually from the appliance.

Figure 13A:
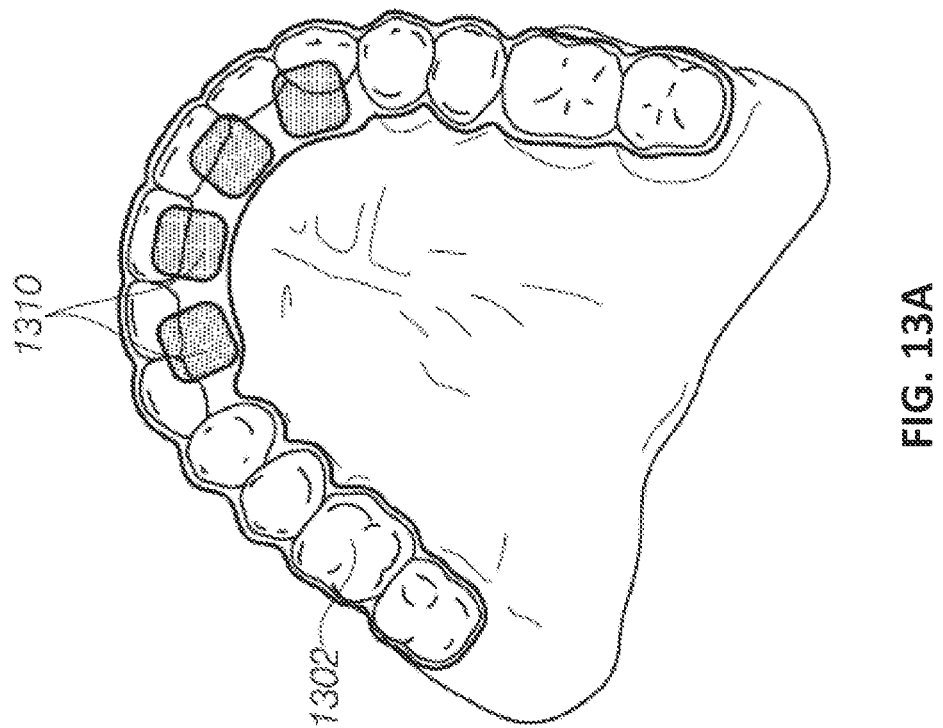
FIGS. 13A-13C illustrates embodiments of aligners having anterior bite ramps.
Figure 13C:
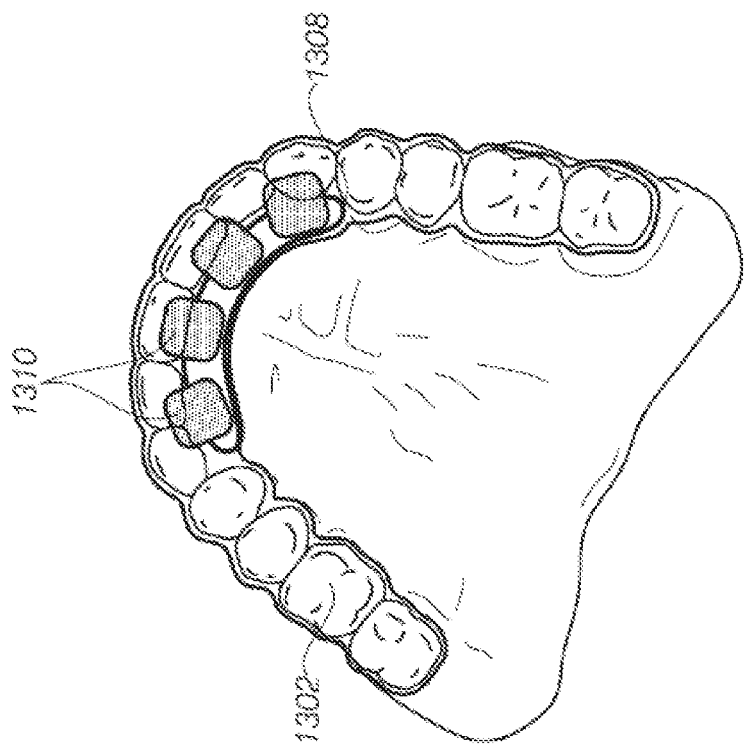
Figure 13B:
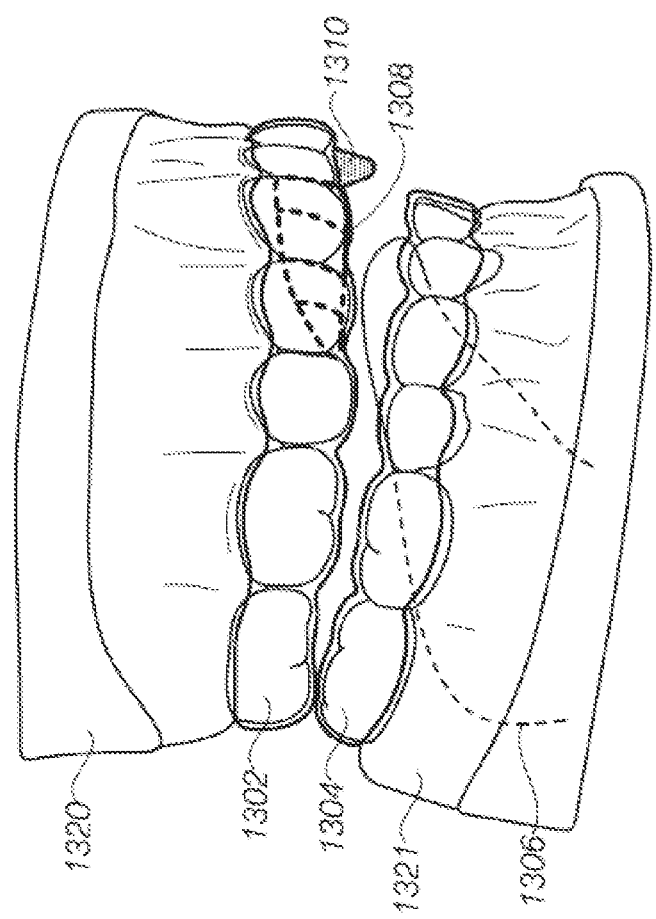

Barrier portions can also be advantageous in embodiments of aligners 1302 in which anterior bite ramps 1310 are used in the upper lingual area, as shown in FIG. 13A. In such embodiments, the addition of a barrier can be desirable in order to form a seal with the tongue and reduce or prevent air leakage. Anterior bite ramps are often used when treating patients with a deep bite and an accentuated curve of Spee, and this curve often leads to a lateral opening prone to air leakage when the lower jaw is advanced forward. FIG. 13B illustrates embodiments of an upper aligner 1302 and a lower aligner 1304. FIG. 13B shows a side view of both aligners in the mouth (shown on a partial sectional view of a patient's mouth or a model of a patient's upper and lower jaws, for simplicity). In FIG. 13B, the barrier 1308 is in front of the anterior bite ramp 1310. The lower jaw 1321 may slide forward (anteriorly) and rest on the anterior vertical stops (bite ramps 1308) which may also contain a barrier portion to block air leakage. FIG. 13C shows a bottom view of the upper aligner 1302. The upper aligner 1302 comprises anterior bite ramps 1310 and a barrier potion 1308.

When implementing the treatments described herein, customized aligners can be used. A simulation of an aligner including features can be placed over the thickness of the teeth. The simulated aligner can include any features used by the patient, such as bite ramps or bite repositioners. The effect of the aligner on the bite is observed in the simulation. Virtual, digital modeling can show the bite angle changes using, for example, a virtual articulator, which can, in turn, show how much the bite opening changes the vertical dimension. Based on such a simulation, a barrier feature can be created to return the bite to a normal vertical dimension.

Generally, the goal is for the barrier portion to extend vertically and create an artificial overbite. In some embodiments, the barrier portion may have to expand beyond the perimeter of the arch. The patient's facial shape may influence the configuration of the barrier portion. Jaw angle can correspond to face shape. For example, a long facial profile (i.e., dolichofacial) can comprise a downward sloping angle in the lower jaw, while a short, square face pattern (i.e., brachyfacial) can comprise a more parallel angle between the lower and upper jaws. In patients with the long facial pattern, the downward sloping angle of the mandible can exaggerate any opening caused by a thickness on the occlusal surfaces of the back teeth. In such cases, the barrier portion can utilize a tapering height to avoid adding any thickness to the aligners in the posterior regions near the terminal ends. For example, the barrier extension can be 3 mm vertical in the front, but taper to 0 mm in height closer towards the back teeth of the dental arch.

A patient may receive an orthodontic treatment course with a series of aligners, for example 20-40 aligners. New sets of aligners can be provided to the patient by the doctor every few weeks. Each aligner is configured to provide orthodontic forces which gradually move the teeth. The barrier portions may be provided in a first subset (e.g., the first 5-10 aligners) of the series, and not be provided in the aligners to be used later.

The barrier portion can be manufactured as part of the aligner, similar to aligner ridges and bite ramps. Alternatively, the barrier portion can be a piece that is manufactured separately (e.g. 3-D printed, milled, or injection molded) and then connected to the aligner in a separate manufacturing step (with adhesive, spot welding, ultrasonic welding, etc.). Alternatively, the barrier portion can be 3-D printed in a different material in the case of 3-D printed aligner appliances. This avoids needing a separate manufacturing step to connect the barrier portion to the aligner appliance.

When a barrier is included as part of aligner in a series of aligners, the position and/or size of the barrier may change within the series. For example, the initial aligners in the series may include a barrier (or a larger barrier); the barrier may be smaller, reducing in size, or absent from subsequent aligners in the series.

The location and thickness of the barrier portion can be important. The greater the amount of surface area engagement of the aligner with the teeth, the more effective the tooth movement. Thus, it can be undesirable for the barrier portion to prevent or reduce the aligner's interaction with the teeth. A possible solution for this problem is to form the barrier portion as thinly as possible so that the base of the barrier covers as much of the dentition as possible. To ensure structural integrity of the barrier despite its thinness, the aligner can be fabricated from a refractory reference mold which contains structural support tabs that break away from the mold when the aligner is separated from the mold during the fabrication process. In other words, the tabs built into the mold via 3-D printing, stereolithography, or milling, separate from the mold and become embedded inside the aligner barrier portion in order to confer extra structural support to the aligner barrier feature. These embedded features are not limited to plastic materials, but can include metals, carbon fiber, and/or ceramics, given that many different types of materials besides plastic can now be 3-D printed as the refractory mold. Thus, in any of the devices described herein, the barrier may include a reinforcing support within the barrier, and this reinforcing support may be formed by support features that break away from the reference mold to become embedded inside the aligner barrier feature during the manufacturing process.

While many of the embodiments described herein have been applied to cases of anterior open bite, the same principles also apply to lateral open bite. The barrier portions could be applied to posterior regions of the aligner in such cases, either unilaterally or bilaterally. Furthermore, in some embodiments, the aligner and barrier portions can be used as standalone therapy for speech impediments, and not just for orthodontic treatments, as some patients may have trouble forming a proper seal with their mouth while speaking, even without an orthodontic appliance in place.

Figure 14:
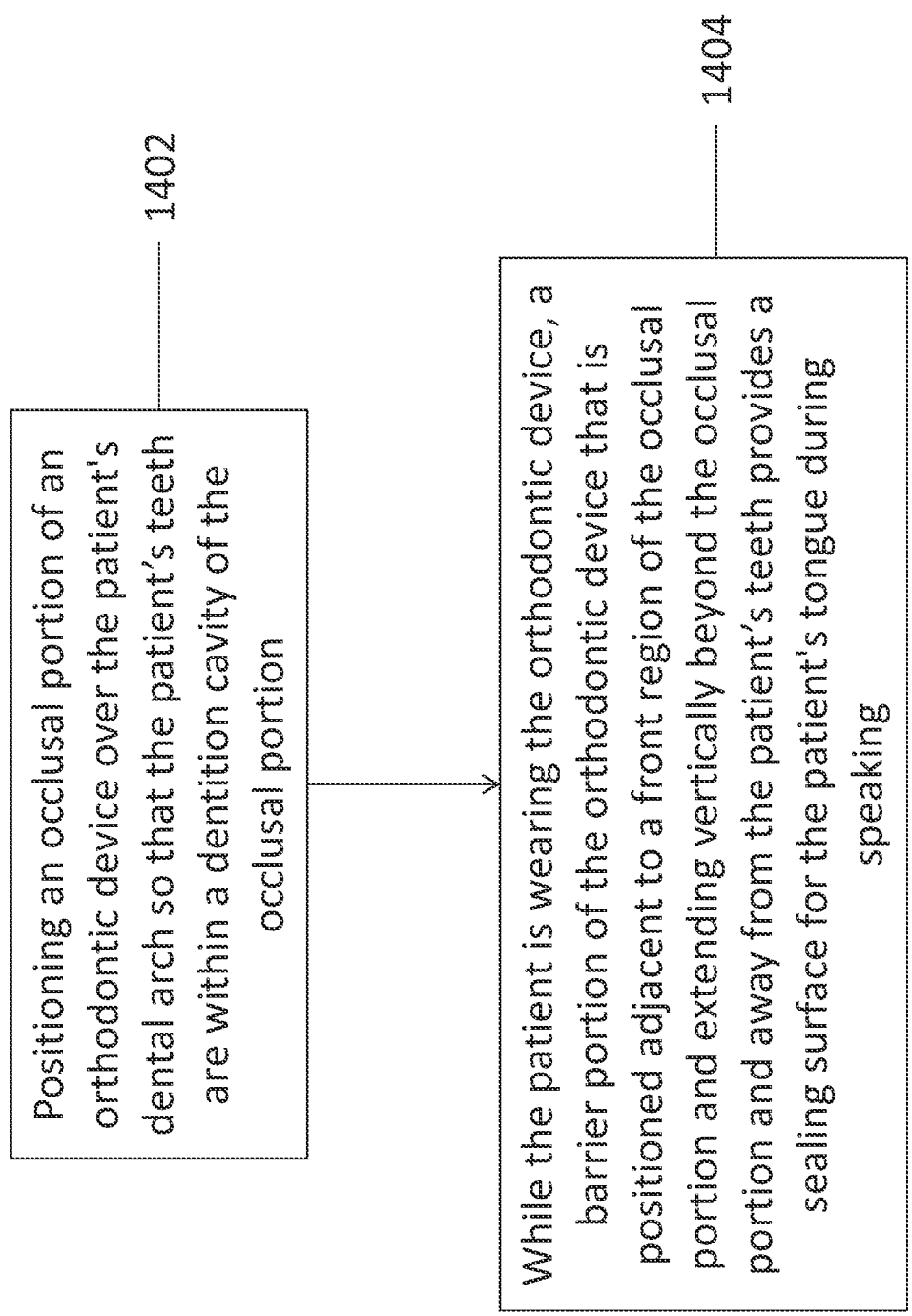
FIG. 14 illustrates an embodiment of a method of orthodontic treatment.

FIG. 14 shows an embodiment of a method of orthodontic treatment using devices such as those disclosed herein. As shown at block 1402, the method comprises positioning an occlusal portion of an orthodontic device over the patient's dental arch so that the patient's teeth are within a dentition-receiving cavity of the occlusal portion. As shown at block 1404, while the patient is wearing the orthodontic device, a barrier portion of the orthodontic device that is positioned adjacent to a region of the occlusal portion and extending vertically beyond the occlusal portion and away from the patient's teeth provides a sealing surface for the patient's tongue during speaking.

FIG. 15 depicts another embodiment of a method of orthodontic treatment using devices such as those disclosed herein. As shown at block 1502, the method comprises positioning an occlusal portion of an orthodontic device over the patient's dental arch so that the patient's teeth are within a dentition-receiving cavity of the occlusal portion to apply force to the patient's teeth to align the teeth by gradually moving the patient's teeth relative to each other when the orthodontic device is worn. As shown at block 1504, while the patient is wearing the orthodontic device, a barrier portion of the orthodontic device that is positioned adjacent to a region of the occlusal portion and extending vertically beyond the occlusal portion and away from the patient's teeth provides a sealing surface for the patient's tongue during speaking.

Figure 16:
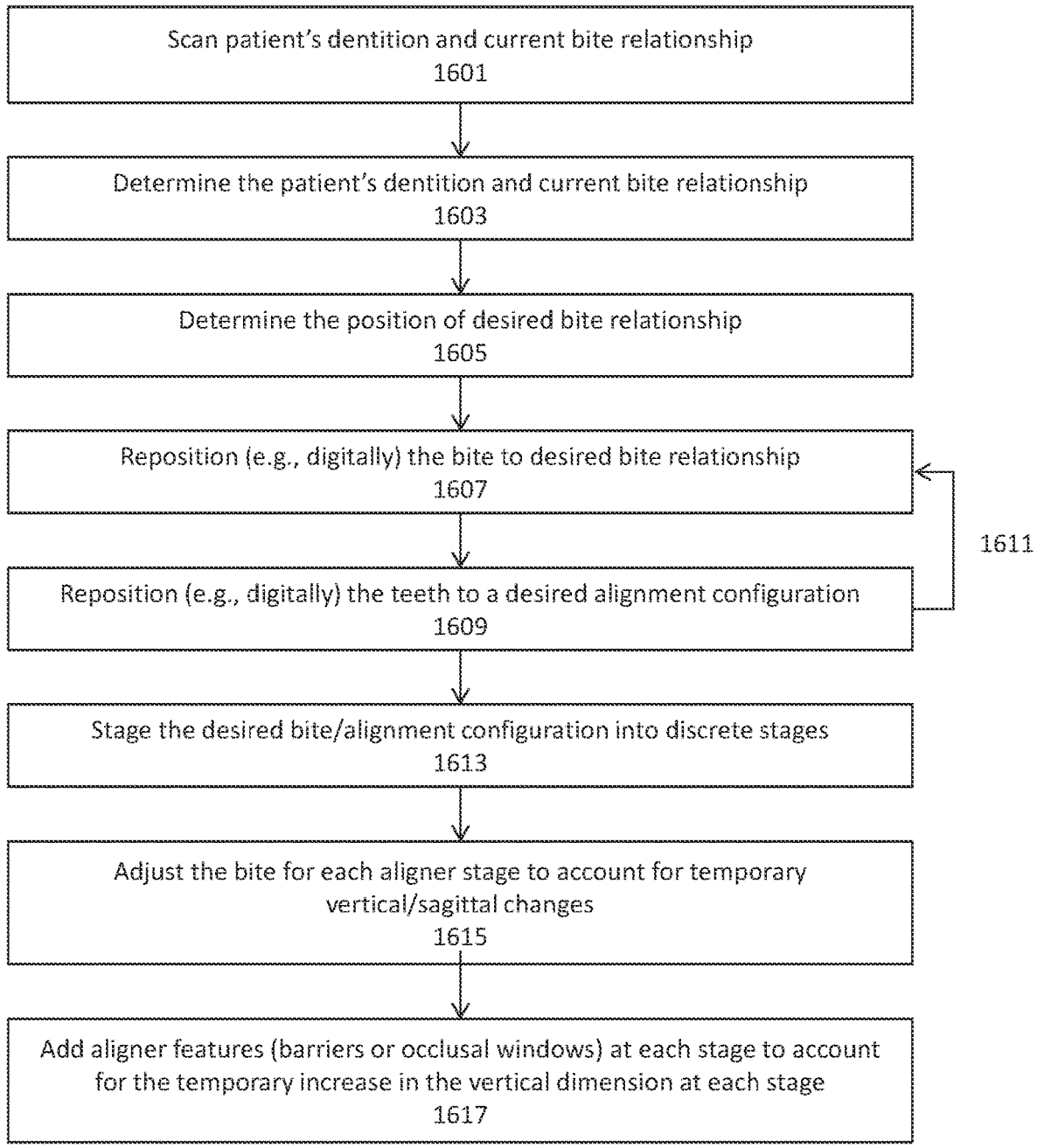
FIG. 16 illustrates a method for determining dimensions of a barrier portion of an orthodontic device as described herein.

Also described herein are methods of determining the dimensions of the barrier portion included as part of an aligner apparatuses described herein (or as part of an apparatus that is not configured to align the teeth). FIG. 16 is a schematic flow diagram illustrating a method of determining the dimensions of a barrier in an aligner apparatus. This method may be modified as necessary to determine the dimensions of a barrier for a device that is not also configured as an aligner, by omitting those steps not necessary to re-align the teeth. The models of the patient's dentition (including dimensions) may be made manually and/or electronically. For example, as shown in FIG. 16, the patient's dentition may be initially scanned 1601 or otherwise determined (e.g., using dental impressions, photographic or radiographic images, models, direct measurements, etc.). The patient's dentition may be scanned to determine the patient's dentition and current bite relationship 1603, or the bite relationship (e.g., between the teeth of the upper and lower jaws) may be otherwise determined. Next, the position of desired bite relationship is determined (e.g., Class 1 molar and canine relationship). This may be determined by scanning (e.g., the patient's mouth or a model of the dentition) the position of the desired bite relationship. For example, in a Class 2 patient, the lower jaw can be protruded and the teeth scanned in the "protruded" Class 1 bite relationship. In another example, in a Class 3 patient, physical models of the arches can be repositioned into a Class 1 relationship and the model relationship digitally captured. As an alternative to capturing altered physical bite relationships, the target bite may also be determined by digitally manipulating a digital representation of the patient's arches into the desired bite relationship. The goal in all of these manipulations is to create a model of the bite in a desired bite relationship 1607. Next, the teeth in the models of the arches may be repositioned to determine a desired relationship goal 1609. For example, the teeth may be digitally repositioned to determine a desired alignment configuration. These steps (1607, 1609) may be repeated 1611 until a desired setup of bite relationship/teeth alignment combination is achieved.

The desired movements of the teeth and/or changes in the bite from initial to goal may then be staged in discrete steps or stages, each step/stage representing an individual set of upper and lower aligners 1613. Thereafter, the bite position can be adjusted (e.g., digitally) for each aligner stage to account for temporary vertical/sagittal changes due to the repositioned teeth/bite, aligner thickness, bite repositioning aligner features, anterior bite ramp features, bite blocks, etc. 1615. Thereafter, aligner features (such as barriers or occlusal windows) may be added (e.g., digitally) at each stage to account for the temporary increase in the vertical dimension at each stage due to the aligner thickness and/or additional aligner features present 1617. Each aligner designed in this manner may then be manufactured (e.g., as described herein) and provided to the patient for treatment.

Figure 18:
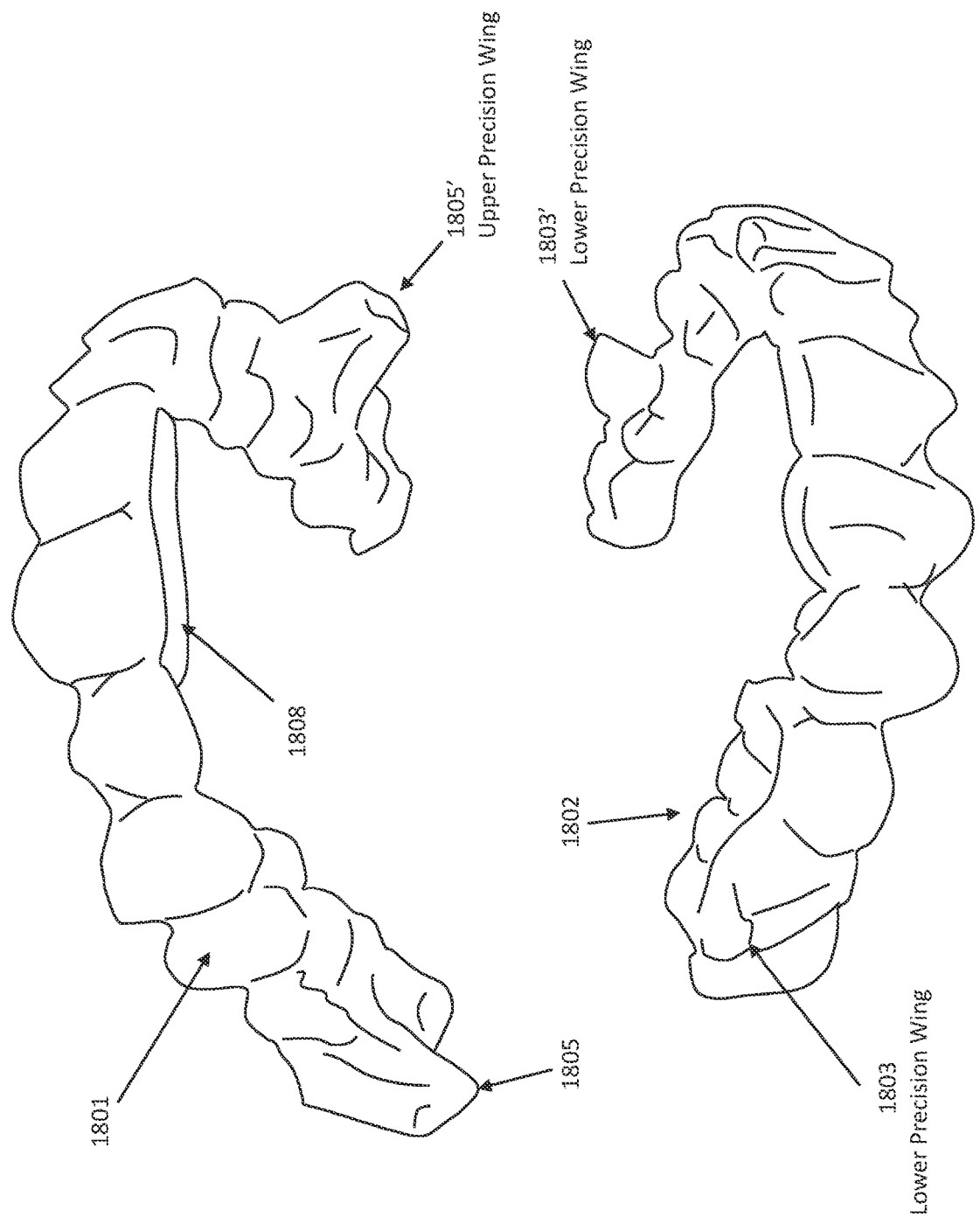
FIG. 18 illustrates another example of an orthodontic appliance including a barrier portion to enhance speech and/or patient comfort.

FIG. 18 is another example of an apparatus including a barrier portion extending laterally and adjacent to an occlusal portion. In this example the apparatus includes an upper appliance 1801 (upper arch appliance) and a lower appliance 1802 (lower arch appliance) that are configured to be worn over the patient's upper and lower arch, respectively. The upper and lower appliances in this example are configured as a mandibular advancement apparatus, in which each of the upper and lower appliances include wings that may engage with each other to drive the lower jaw forward during treatment when worn. For example, the upper arch appliance 1801 includes a first upper precision wing 1805' on a left sides and a second upper precision wing 1805 on the right side. The lower arch appliance may include a pair of wings (e.g., lower precision wings 1803, 1803') that may engage with each other to advance the patient's mandible. In FIG. 18, the upper arch appliance also includes a barrier 1808 (barrier portion). Alternatively or additionally, the lower arch appliance may include a barrier. In this example, the appliance(s) are formed as shell appliances that may also be configured to apply force to move the teeth. In some variation, the appliances are not configured to move individual teeth, but may be configured for mandibular advancement. When a patient is wearing the apparatus of FIG. 18, the upper and lower appliances may be worn together, so that when the patient's mouth is closed, the upper appliance may engage with the lower appliance, driving the lower appliance forward to advance the mandible; a seal may be formed between the patient's tongue and the barrier 1808, as air may be prevented from passing through the region. As described above, this may enhance comfort and may also prevent lisping or other speech difficulties.

In any of the appliance variations in which bite correction features are included (e.g., bite ramps, wings, etc.), the appliance(s) may include any of the features described herein, such as barriers and/or thinned or removed peak occlusal surface portions. In particular, any treatment and/or apparatus that tends to open the bite may benefit from an anterior compensation for speech enhancement as described herein, in order to avoid lisping in the patient. For example, appliances including a bite ramp, and/or variable thickness appliance, such as aligners.

Figure 19A:
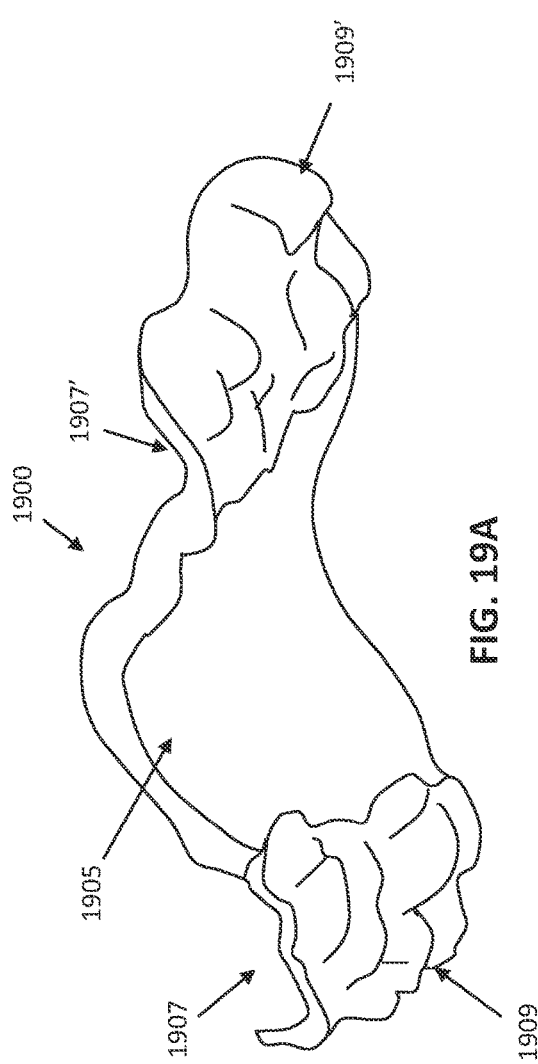
FIGS. 19A-19B illustrates an example of another orthodontic appliance that may be configured to include (as shown in FIG. 19B) a barrier portion to enhance speech and/or patient comfort.

Another example of an apparatus that may be configured to enhance speech (e.g., preventing lisping, etc.) is shown in FIG. 19A. FIG. 19A shows one in a series of palatal expanders 1900 that may be worn by a subject to expand the subject's palate (e.g., by widening the suture). Although any appropriate palatal expander may be used (including adjustable/expandable variations) the apparatus shown in FIG. 19A may be worn as part of a series of palatal expanders worn sequentially to adjust the width of the palate.

Figure 19B:
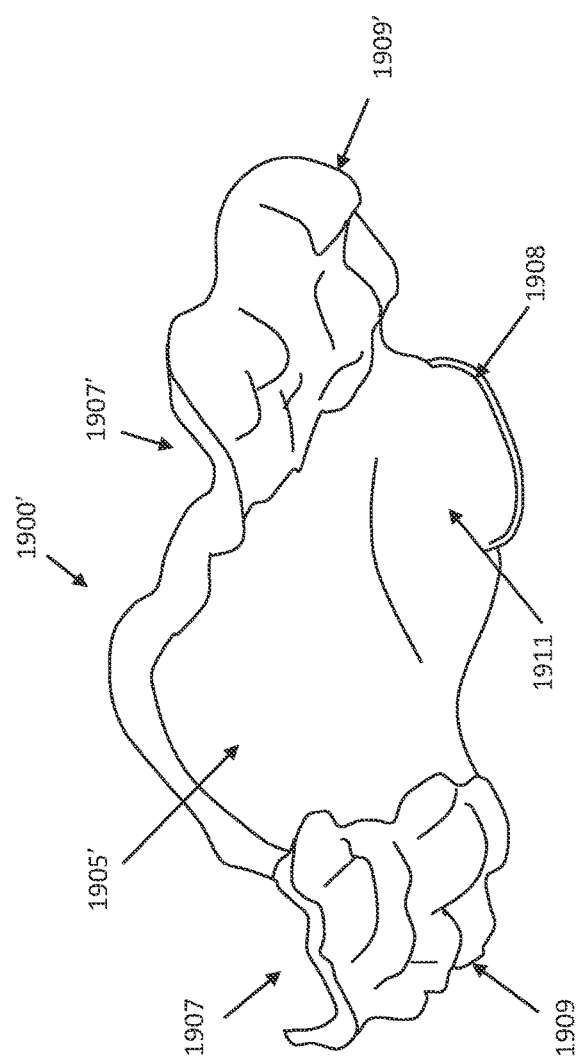

FIG. 19B shows a variations of the palatal expander of FIG. 19A with a barrier region 1908 at the anterior (front) end of the apparatus. In general, the palatal expander includes an occlusal portion having a dentition-receiving cavity 1907, 1907' extending laterally in an arch and having a first vertical height. In FIGS. 19A and 19B, the occlusal portion includes two dentition-receiving cavities, holding the molar and premolars; a palatal region 1905 extends lateral to the occlusal portion, e.g., between the first and second dentition-receiving cavities 1907, 1097'. Each dentition-receiving cavity is configured to fit over a portion of the patient's dental arch (e.g., the pre-molar and molars), and the dentition-receiving cavity may include an occlusal surface section adapted to be positioned over an occlusal surface of the patient's teeth. In FIG. 19B, the apparatus includes a barrier region 1908 that extends anteriorly from the palatal region on an extension or neck region 1911. The barrier portion therefore also extends laterally and adjacent to the occlusal portion, as descried above. The barrier portion may have a vertical height that is approximately the same height or a greater height than the maximum vertical height of the outer occlusal surface of the apparatus. As in any of these variations, the barrier portion may be laterally continuous to reduce or prevent air leakage, so that a patient's tongue may form a seal against the barrier portion when the patient is speaking while wearing the device.

Any of these apparatuses described herein may be used when the molars/premolars have a reduced height. For example, in some patients having bruxism (e.g., due to grinding of teeth), wearing down of the rear teeth, the jaw may overdose, resulting in a deep bite that may also lead to wear of the front teeth. Appliances to address this, including via restorative dentistry and/or the use of appliances (e.g., a series of aligners) to adjust the teeth, including straightening them, prior to placing restorative crowns on the teeth. Any of these appliances may include the structures, and particularly an anterior barrier structure, to enhance speech. Any of the methods, systems and/or components described herein (including U.S. Pat. No. 8,936,463, showing aligners with images of the target alignment shown on them). The methods and apparatuses described herein may prevent or limit leakage, including buccal leakage, through the apparatus.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An orthodontic aligner device that prevents lisping, the device comprising:
   an aligner body having:
   a dentition-receiving cavity shaped to fit over at least a portion of a dental arch of a patient, and configured to apply a force to a first set of the patient's teeth within the dentition-receiving cavity;
   a plurality of lateral wall surfaces shaped to be placed in contact with the patient's teeth while the device is worn on the dental arch; and
   a first occlusal cut-out region at a first terminal end of the dental arch and a second occlusal cut-out region at a second terminal end of the dental arch;
   wherein the first occlusal cut-out region and the second occlusal cut-out region are surrounded by one or more lateral wall surfaces of the plurality of lateral wall surfaces with the occlusal surfaces of the patient's molars exposed and able to touch the opposing arch while the device is worn over the patient's teeth;

wherein the dentition-receiving cavity includes a plurality of upper surface sections arranged to be positioned over occlusal surfaces of the patient's teeth while the device is worn on the dental arch, wherein a thickness of the upper surface sections is thinner near the first and second terminal ends of the dental arch, and gets thicker towards a middle region between the first and second terminal ends of the dental arch; and wherein the first occlusal cut-out region and the second occlusal cut-out region expose occlusal surfaces of the patient's rear teeth to form an anterior seal between the patient's tongue and inner surfaces of the patient's anterior teeth in a manner as to minimize any anterior bite opening, preventing lisping while the device is worn over the dental arch.

2. The device of claim 1, wherein the first or second occlusal cut-out region extends over two or more teeth while the device is worn over the dental arch.

3. The device of claim 1, wherein the first or second occlusal cut-out region extends over three or more teeth while the device is worn over the dental arch.

4. The device of claim 1, wherein the first and second occlusal cut-out regions extend into the lateral wall surfaces of the portion of the dentition-receiving cavity adjacent to the patient's molars while the device is worn over the dental arch.

5. The device of claim 1, further comprising a plurality of interproximal supports between buccal and lingual surfaces of the lateral wall surfaces.

6. An orthodontic aligner device that prevents lisping, the device comprising:

an aligner body having a dentition-receiving cavity shaped and sized to fit over at least a portion of a dental arch of a patient and configured to apply orthodontic force to the patient's teeth within the dentition-receiving cavity to gradually align the patient's teeth, the dentition-receiving cavity including a posterior teeth region having lateral walls configured to receive the patient's posterior teeth, wherein the posterior teeth region includes occlusal cut-outs that are configured to expose occlusal surfaces of at least a portion of the patient's posterior teeth and allow opposing occlusal surfaces of the patient's posterior teeth to come close enough to touch each other while the device is worn over the dental arch to form an anterior seal between the patient's tongue and inner surfaces of the patient's anterior teeth in a manner as to minimize any temporary anterior bite opening, preventing lisping while the device is worn over the dental arch.

7. The device of claim 6, wherein the posterior teeth region is configured to receive the patient's molars, pre-molars, or molars and pre-molars.

8. The device of claim 6, wherein the dentition-receiving cavity is configured to receive one or more of the patient's anterior teeth.

9. An orthodontic aligner device that prevents lisping, the device comprising:

an aligner body having a dentition-receiving cavity shaped and sized to fit over at least a portion of a dental arch of a patient and configured to apply orthodontic force to the patient's teeth within the dentition-receiving cavity to gradually align the patient's teeth, the dentition-receiving cavity including a posterior teeth region having lateral walls configured to receive the patient's posterior teeth, the posterior teeth region including occlusal cut-outs that are configured to expose occlusal surfaces of at least a portion of the patient's posterior teeth and allow opposing occlusal surfaces of the patient's posterior teeth to touch each other while the device is worn over the dental arch to form an anterior seal between the patient's tongue and inner surfaces of the patient's anterior teeth in a manner as to minimize any anterior bite opening, preventing lisping while the device is worn over the dental arch, wherein at least two of the occlusal cut-outs are separated by an interproximal support that extends between a buccal side and a lingual side of the posterior teeth region.

\* \* \* \* \*